United States Patent
Lu et al.

(10) Patent No.: US 9,903,823 B2
(45) Date of Patent: Feb. 27, 2018

(54) METROLOGY METHOD AND APPARATUS

(71) Applicant: ASML NETHERLANDS B.V., Veldhoven (NL)

(72) Inventors: Yen-Wen Lu, Saratoga, CA (US); Jay Jianhui Chen, Fremont, CA (US); Wei Liu, Los Altos, CA (US); Boris Menchtchikov, Cupertino, CA (US); Jen-Shiang Wang, Sunnyvale, CA (US); Te-Chih Huang, Hsinchu (TW)

(73) Assignee: ASML NETHERLANDS B.V., Veldhoven (NL)

( * ) Notice: Subject to any disclaimer, the term of this patent is extended or adjusted under 35 U.S.C. 154(b) by 168 days.

(21) Appl. No.: 14/945,257

(22) Filed: Nov. 18, 2015

(65) Prior Publication Data
US 2016/0146740 A1 May 26, 2016

Related U.S. Application Data

(60) Provisional application No. 62/082,987, filed on Nov. 21, 2014.

(51) Int. Cl.
*G01N 21/88* (2006.01)
*G01B 11/27* (2006.01)
(Continued)

(52) U.S. Cl.
CPC ....... *G01N 21/8806* (2013.01); *G01B 11/272* (2013.01); *G01N 21/9501* (2013.01);
(Continued)

(58) Field of Classification Search
None
See application file for complete search history.

(56) References Cited

U.S. PATENT DOCUMENTS 8,411,287 B2   4/2013   Smilde et al.
8,749,786 B2 *   6/2014   Fuchs .................. G01N 21/956
                                                                                                                  356/401
(Continued)

FOREIGN PATENT DOCUMENTS

WO    2009/078708    6/2009
WO    2009/106279    9/2009
WO    2011/012624    2/2011

OTHER PUBLICATIONS

International Search Report dated Mar. 23, 2016 in corresponding International Patent Application No. PCT/EP2015/074460.

*Primary Examiner* — Shawn Decenzo
(74) *Attorney, Agent, or Firm* — Pillsbury Winthrop Shaw Pittman LLP

(57) ABSTRACT

A method to determine an overlay error between a first structure and a second structure, wherein the first structure and second structures are on different layers on a substrate and are imaged onto the substrate by a lithographic process, the method comprising: obtaining an apparent overlay error; obtaining a systematic error caused by a factor other than misalignment of the first and second structures; and determining the overlay error by removing the systematic error from the apparent overlay error. The method may alternatively comprise obtaining apparent characteristics of diffraction orders of diffraction by an overlapping portion of the first and second structures; obtaining corrected characteristics of the diffraction orders; determining the overlay error from the corrected characteristics; and adjusting a characteristic of the lithographic process based on the overlay error.

20 Claims, 14 Drawing Sheets

(51) Int. Cl.
  *G03F 7/20* (2006.01)
  *G01N 21/95* (2006.01)
(52) U.S. Cl.
  CPC ...... *G03F 7/70516* (2013.01); *G03F 7/70633* (2013.01); *G03F 7/70683* (2013.01); *G01N 2021/8822* (2013.01)

(56) References Cited

U.S. PATENT DOCUMENTS

| | | |
|---|---|---|
| 8,767,183 B2 | 7/2014 | Den Boef |
| 8,867,020 B2 | 10/2014 | Smilde et al. |
| 8,908,147 B2 | 12/2014 | Den Boef et al. |
| 9,081,303 B2 | 7/2015 | Cramer et al. |
| 9,134,256 B2 | 9/2015 | Smilde et al. |
| 2010/0321654 A1 | 12/2010 | Den Boef |
| 2011/0027704 A1 | 2/2011 | Cramer et al. |
| 2011/0043791 A1 | 2/2011 | Smilde et al. |
| 2012/0013881 A1* | 1/2012 | Den Boef .............. G03B 27/52 355/67 |
| 2012/0242970 A1 | 9/2012 | Smilde et al. |
| 2012/0244461 A1* | 9/2012 | Nagai ................. G03F 7/70525 430/30 |
| 2013/0258310 A1 | 10/2013 | Smilde et al. |
| 2014/0176965 A1 | 6/2014 | Fuchs et al. |

* cited by examiner

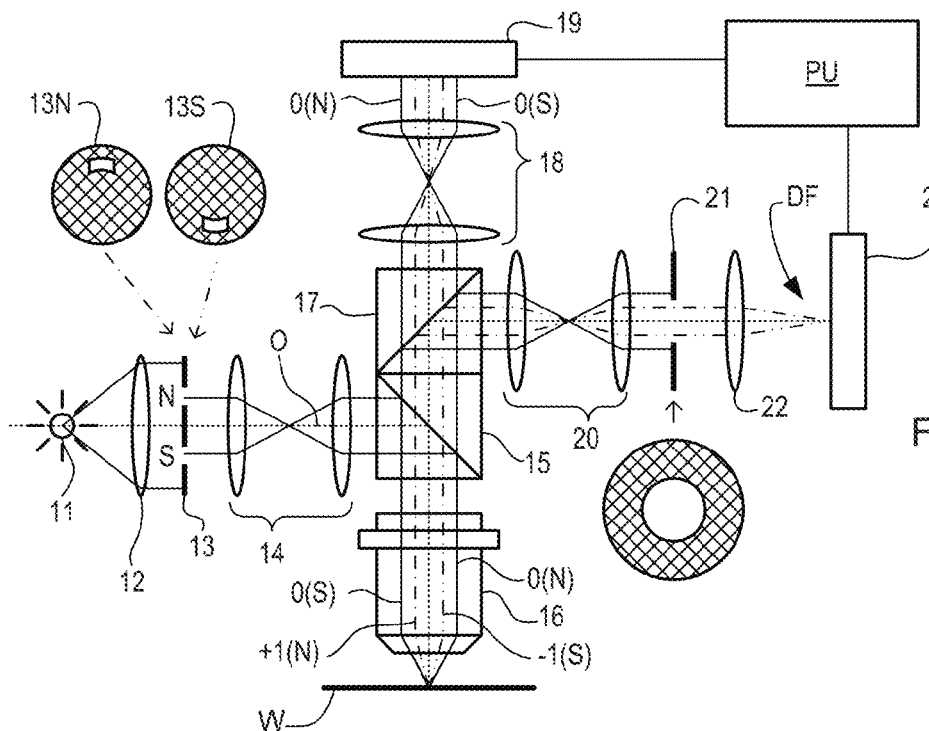
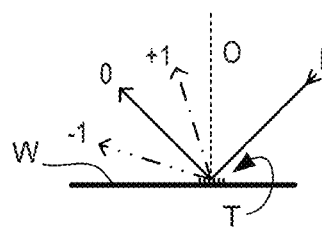 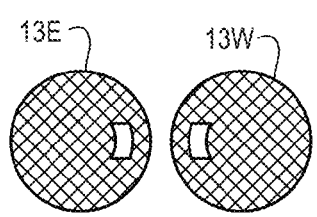 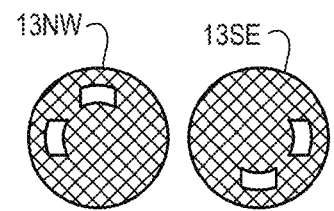
Fig. 3(B)  Fig. 3(C)  Fig. 3(D)
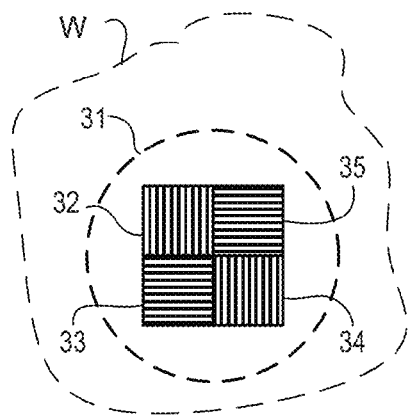 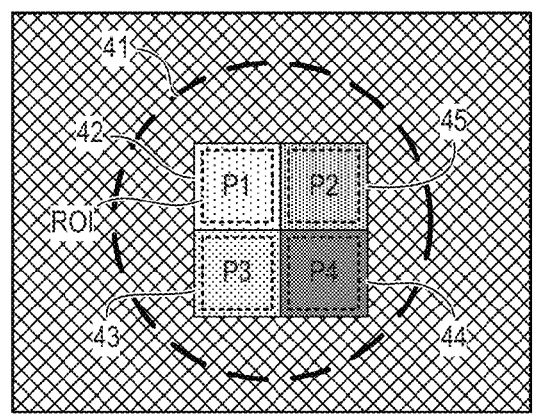
Fig. 4  Fig. 5

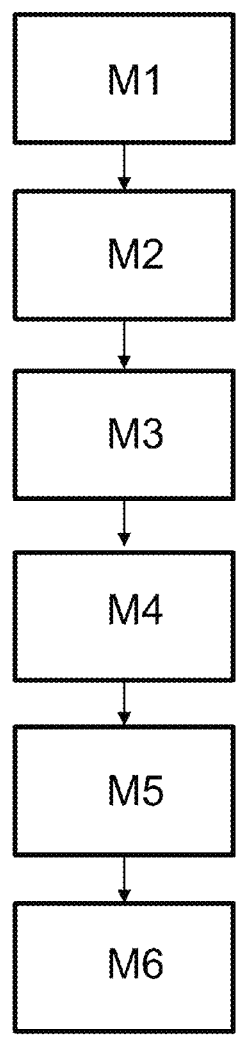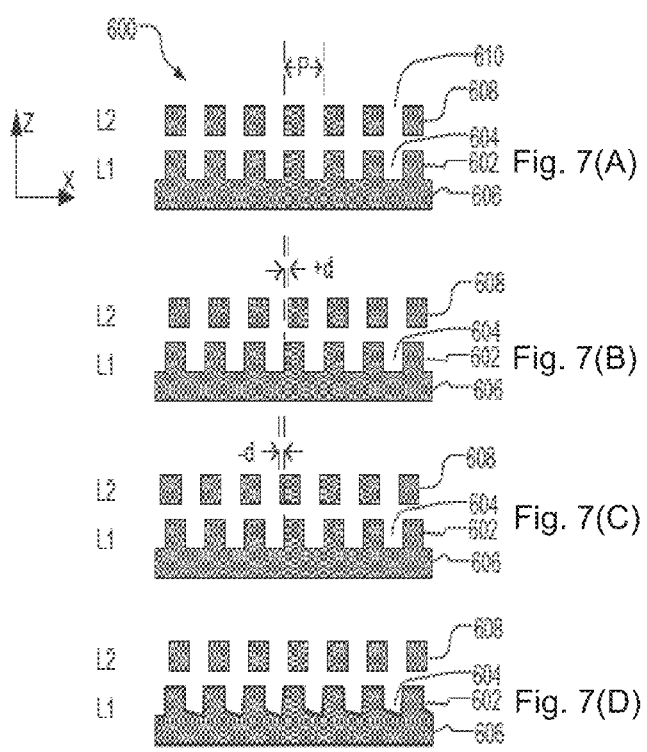
Fig. 6
Fig. 7(A)
Fig. 7(B)
Fig. 7(C)
Fig. 7(D)

METROLOGY METHOD AND APPARATUS

This application claims the benefit of priority of U.S. provisional patent application No. 62/082,987, filed Nov. 21, 2014, which is incorporated herein in its entirety by reference.

TECHNICAL FIELD

The description herein relates to lithographic apparatuses and processes, and more particularly to a method or tool for characterizing overlay in a lithographic process.

BACKGROUND

A lithographic apparatus can be used, for example, in the manufacture of integrated circuits (ICs) and other devices. In such a case, a patterning device (e.g., a mask) may contain or provide a pattern corresponding to an individual layer of the device ("design layout"), and this pattern can be transferred onto a target portion (e.g. comprising one or more dies) on a substrate (e.g., silicon wafer) that has been coated with a layer of radiation-sensitive material ("resist"), by methods such as irradiating the target portion through the pattern on the patterning device. In general, a single substrate contains a plurality of adjacent target portions to which the pattern is transferred successively by the lithographic apparatus, one target portion at a time. In one type of lithographic apparatuses, the pattern is transferred onto one target portion in one go; such an apparatus is commonly referred to as a wafer stepper. In an alternative apparatus, commonly referred to as a step-and-scan apparatus, a projection beam scans over the patterning device in a given reference direction (the "scanning" direction) while synchronously moving the substrate parallel or anti-parallel to this reference direction. Different portions of the pattern on the patterning device are transferred to one target portion progressively. Since, in general, the lithographic apparatus will have a magnification factor M (generally <1), the speed F at which the substrate is moved will be a factor M times that at which the beam scans the patterning device.

Prior to transferring the pattern from the patterning device to the substrate, the substrate may undergo various procedures, such as priming, resist coating and a soft bake. After exposure, the substrate may be subjected to other procedures, such as a post-exposure bake (PEB), development, a hard bake and measurement/inspection of the transferred pattern. This array of procedures is used as a basis to make an individual layer of a device, e.g., an IC. The substrate may then undergo various processes such as etching, ion-implantation (doping), metallization, oxidation, chemo-mechanical polishing, etc., all intended to finish off the individual layer of the device. If several layers are required in the device, then the whole procedure, or a variant thereof, is repeated for each layer. Eventually, a device will be present in each target portion on the substrate. These devices are then separated from one another by a technique such as dicing or sawing, whence the individual devices can be mounted on a carrier, connected to pins, etc.

As noted, lithography is a central step in the manufacturing of ICs and other devices, where patterns formed on substrates define functional elements of the devices, such as microprocessors, memory chips etc. Similar lithographic techniques are also used in the formation of flat panel displays, micro-electro mechanical systems (MEMS) and other devices.

In a lithographic process (i.e., a process of developing a device or other structure involving lithographic exposure, which may typically include one or more associated processing steps such as development of resist, etching, etc.), it is desirable frequently to make measurements of structures created, e.g., for process control and verification. Various tools for making such measurements are known, including scanning electron microscopes, which are often used to measure critical dimension (CD), and specialized tools to measure overlay, the accuracy of alignment of two layers of a substrate.

SUMMARY

Device manufacturers align substrates using targets (marks) that are present on a substrate. For example, an alignment sensor measures the location of the mark with sub-nm repeatability.

But, a complexity in lithography is overlay error. A microscopic device (e.g., an IC) may include multiple layers of patterns during and after its manufacturing process. For example, the multiple layers of patterns may include undeveloped and developed patterns exposed into a resist layer, patterns of metals and non-metals, or patterns etched into a layer of material. Not only the shapes and positions of the patterns within a layer affect the function of the device, but also the relative positions of the patterns in different layers. Patterns in different layers should be aligned—i.e., their relative positions in directions parallel to the substrate should be within a determined range. Misalignment can cause device failures such as short circuits and broken connection, which in turn impact fabrication yield and profit margins. Errors in the alignment of patterns in different layers are termed "overlay errors." Here, the term "different layers" does not necessarily require that the layers are different in material; instead, the layers merely are at different depths in a stack of layers on a substrate. The term "undeveloped pattern" in a resist layer means a pattern consisting of exposed portions or unexposed portions in the resist layer but the resist layer has not been subjected to a developer so as to remove the exposed or unexposed portions of the resist layer. An undeveloped pattern may also be called a latent image. The term "developed pattern" in a resist layer means a pattern consisting of removed portions or remaining portions of a resist layer. An undeveloped pattern may become a developed pattern by developing the resist layer (for example by rinsing with an appropriate solvent).

The tolerance for overlay errors decreases with the critical dimension (CD). For example, two features of 100 nm width in adjacent layers may tolerate an overlay error of up to 100 nm before they cease to connect with each other; while two features of 20 nm width can tolerate an overlay error of at most 20 nm. Various techniques may be applied to reduce the overlay error. For example, controlling pattern shift, stability of the lithographic apparatus, placing alignment markers, etc. These techniques benefit from a metrology solution for measuring overlay errors because measuring the overlay errors can both verify the effect of these techniques and adjust parameters of these techniques. A good metrology solution may have the traits of being fast, non-destructive, in-line (i.e., without pulling a substrate out of the fabrication flow), and artifact tolerant.

Thus, manufacturers may measure, for example, on-product overlay using target structures in different layers (e.g., overlapping periodic structures). One type of metrology solution for overlay errors uses scatterometry to measure radiation scattered off a target structure and determine the overlay error. The target structure can include a grating. The target structure may be in the form of a latent image (i.e., an image in a layer of exposed but undeveloped resist). The ASML YieldStar™ product is an example of the metrology solution for overlay errors.

However, the transverse profile of the structure of the target may have an asymmetry or a shape that affects the measured property. Metrology apparatuses and alignment sensors are sensitive to target structural asymmetry caused by, for example, processing steps like etching, chemical mechanical polishing (CMP), deposition, etc. Such asymmetry leads to measurement errors that are of the order of a few nm's. This effect may start to dominate the position and/or overlay budget and solutions are therefore needed.

It is desirable to provide a method and apparatus for metrology using a target, in which throughput, flexibility and/or accuracy can be improved.

Disclosed herein is a method to determine an overlay error between a first structure and a second structure, wherein the first structure and second structures are on different layers on a substrate and are imaged onto the substrate by a lithographic process, the method comprising: obtaining an apparent overlay error; obtaining a systematic error caused by a factor other than misalignment of the first and second structures; and determining the overlay error by removing the systematic error from the apparent overlay error.

Also disclosed herein is a method to determine an overlay error between a first structure and a second structure, wherein the first structure and second structures are on different layers on a substrate and are imaged onto the substrate by a lithographic process, the method comprising: obtaining an apparent characteristic of diffraction orders of diffraction by an overlapping portion of the first and second structures; obtaining a corrected characteristic of the diffraction order; and determining the overlay error from the corrected characteristic.

Also disclosed herein is a computer program product comprising a computer readable medium having instructions recorded thereon, the instructions when executed by a computer implementing the method of any method disclosed herein.

BRIEF DESCRIPTION OF THE DRAWINGS

The above aspects and other aspects and features will become apparent to those ordinarily skilled in the art upon review of the following description of specific embodiments in conjunction with the accompanying figures, wherein:

FIG. 3(a) is schematic diagram of a dark field measurement apparatus for use in measuring targets according to an embodiment using a first pair of illumination apertures providing certain illumination modes;

FIG. 3(b) is a schematic detail of a diffraction spectrum of a target for a given direction of illumination;

FIG. 3(c) is a schematic illustration of a second pair of illumination apertures providing further illumination modes in using a measurement apparatus for diffraction based overlay measurements;

FIG. 3(d) is a schematic illustration of a third pair of illumination apertures combining the first and second pairs of apertures providing further illumination modes in using a measurement apparatus for diffraction based overlay measurements;

FIG. 4 depicts a form of multiple periodic structure (e.g., multiple grating) target and an outline of a measurement spot on a substrate;

FIG. 5 depicts an image of the target of FIG. 4 obtained in the apparatus of FIG. 3;

FIG. 6 is a flowchart showing the steps of an overlay measurement method using the apparatus of FIG. 3 and adaptable to embodiments of the present invention;

FIGS. 7(a) to 7(d) show schematic cross-sections of overlay periodic structures (e.g., gratings) having different overlay values in the region of zero;

DETAILED DESCRIPTION

Embodiments will now be described in detail with reference to the drawings, which are provided as illustrative examples so as to enable those skilled in the art to practice the embodiments. Notably, the figures and examples below are not meant to limit the scope to a single embodiment, but other embodiments are possible by way of interchange of some or all of the described or illustrated elements. Wherever convenient, the same reference numbers will be used throughout the drawings to refer to same or like parts. Where certain elements of these embodiments can be partially or fully implemented using known components, only those portions of such known components that are necessary for an understanding of the embodiments will be described, and detailed descriptions of other portions of such known components will be omitted so as not to obscure the description of the embodiments. In the present specification, an embodiment showing a singular component should not be considered limiting; rather, the scope is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the scope encompasses present and future known equivalents to the components referred to herein by way of illustration. Before describing embodiments in detail, it is instructive to present an example environment in which embodiments may be implemented.

Figure 1:
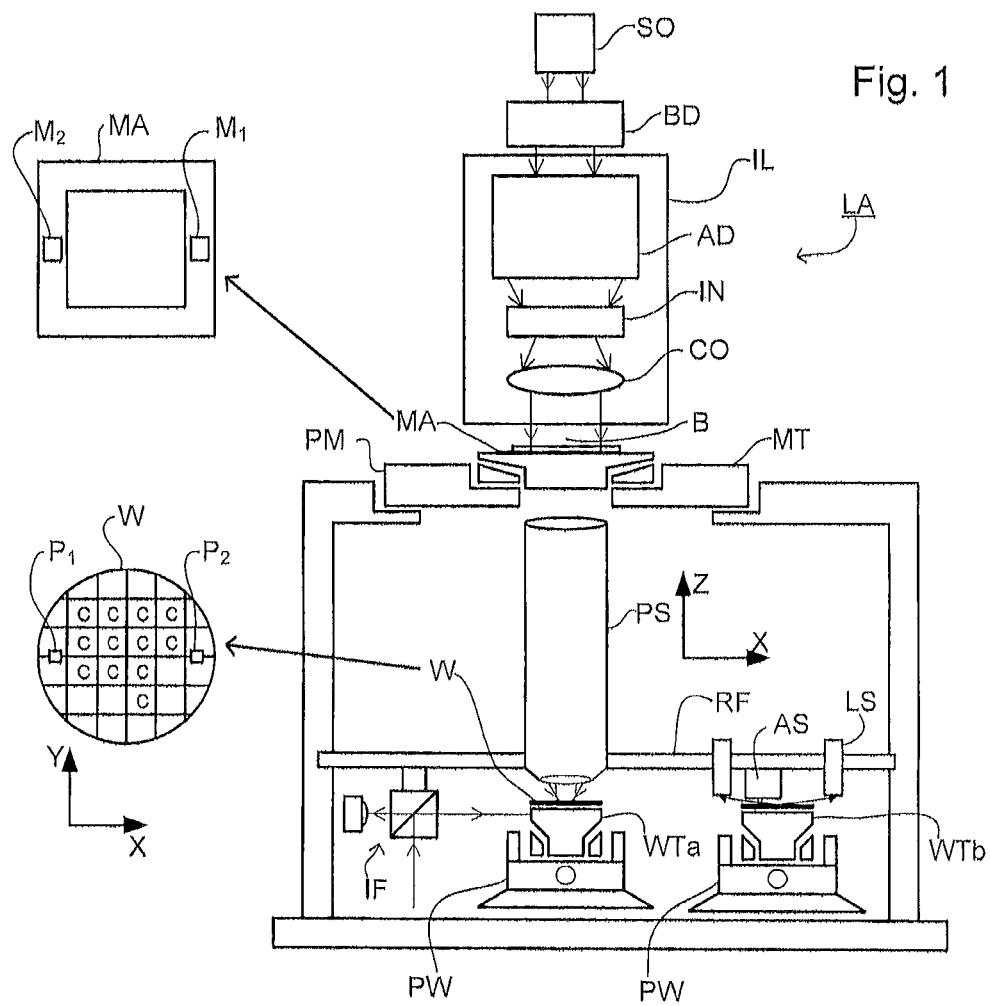
FIG. 1 depicts a lithographic apparatus according to an embodiment.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD configured to adjust the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table MT), and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment markers may also be included within dies, in amongst the device features, in which case it is desirable that the markers be as small as possible and not require any different imaging or process conditions than adjacent features. An embodiment of an alignment system, which can detect the alignment markers, is described further below.

The depicted apparatus could be used in at least one of the following modes:

1. In step mode, the patterning device support (e.g., mask table) MT and the substrate table WTa are kept essentially stationary, while an entire pattern imparted to the radiation beam is projected onto a target portion C at one time (i.e., a single static exposure). The substrate table WTa is then shifted in the X and/or Y direction so that a different target portion C can be exposed. In step mode, the maximum size of the exposure field limits the size of the target portion C imaged in a single static exposure.

2. In scan mode, the patterning device support (e.g., mask table) MT and the substrate table WTa are scanned synchronously while a pattern imparted to the radiation beam is projected onto a target portion C (i.e., a single dynamic exposure). The velocity and direction of the substrate table WTa relative to the patterning device support (e.g., mask table) MT may be determined by the (de)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g., mask table) MT is kept essentially stationary holding a programmable patterning device, and the substrate table WTa is moved or scanned while a pattern imparted to the radiation beam is projected onto a target portion C. In this mode, generally a pulsed radiation source is employed and the programmable patterning device is updated as required after each movement of the substrate table WTa or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Lithographic apparatus LA is of a so-called dual stage type which has two tables WTa, WTb (e.g., two substrate tables) and two stations—an exposure station and a measurement station—between which the tables can be exchanged. For example, while a substrate on one table is being exposed at the exposure station, another substrate can be loaded onto the other substrate table at the measurement station and various preparatory steps carried out. The preparatory steps may include mapping the surface control of the substrate using a level sensor LS and measuring the position of alignment markers on the substrate using an alignment sensor AS, both sensors being supported by a reference frame RF. If the position sensor IF is not capable of measuring the position of a table while it is at the measurement station as well as at the exposure station, a second position sensor may be provided to enable the positions of the table to be tracked at both stations. As another example, while a substrate on one table is being exposed at the exposure station, another table without a substrate waits at the measurement station (where optionally measurement activity may occur). This other table has one or more measurement devices and may optionally have other tools (e.g., cleaning apparatus). When the substrate has completed exposure, the table without a substrate moves to the exposure station to perform, e.g., measurements and the table with the substrate moves to a location (e.g., the measurement station) where the substrate is unloaded and another substrate is load. These multi-table arrangements enable a substantial increase in the throughput of the apparatus.

Figure 2:
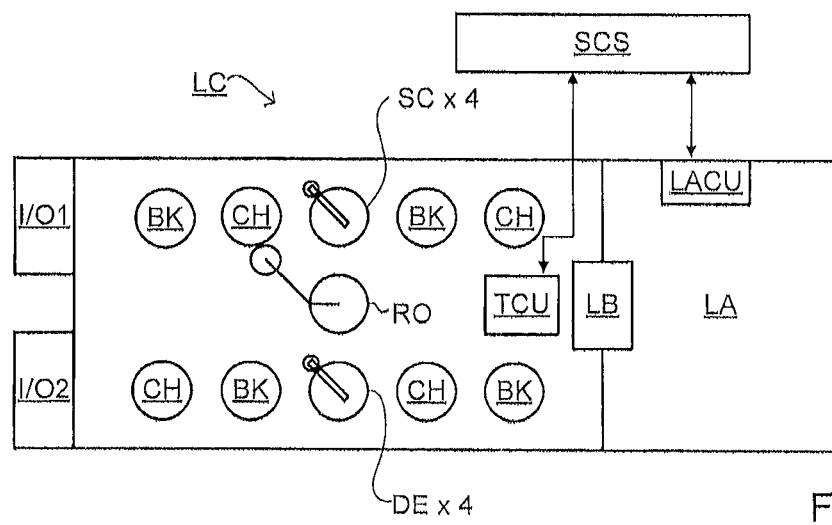
FIG. 2 depicts a lithographic cell or cluster according to an embodiment.

As shown in FIG. 2, the lithographic apparatus LA forms part of a lithographic cell LC, also sometimes referred to as a lithocell or lithocluster, which also includes apparatus to perform one or more pre- and post-exposure processes on a substrate. Conventionally these include one or more spin coaters SC to deposit a resist layer, one or more developers DE to develop exposed resist, one or more chill plates CH and one or more bake plates BK. A substrate handler, or robot, RO picks up a substrate from input/output ports I/O1, I/O2, moves it between the different process devices and delivers it to the loading bay LB of the lithographic apparatus. These devices, which are often collectively referred to as the track, are under the control of a track control unit TCU which is itself controlled by the supervisory control system SCS, which also controls the lithographic apparatus via lithographic control unit LACU. Thus, the different apparatus may be operated to maximize throughput and processing efficiency.

In order that the substrate that is exposed by the lithographic apparatus is exposed correctly and consistently, it is desirable to inspect an exposed substrate to measure one or more properties such as overlay error between subsequent layers, line thickness, critical dimension (CD), etc. If an error is detected, an adjustment may be made to an exposure of one or more subsequent substrates, especially if the inspection can be done soon and fast enough that another substrate of the same batch is still to be exposed. Also, an already exposed substrate may be stripped and reworked (to improve yield) or discarded, thereby avoiding performing an exposure on a substrate that is known to be faulty. In a case where only some target portions of a substrate are faulty, a further exposure may be performed only on those target portions which are good. Another possibility is to adapt a setting of a subsequent process step to compensate for the error, e.g. the time of a trim etch step can be adjusted to compensate for substrate-to-substrate CD variation resulting from the lithographic process step.

An inspection apparatus is used to determine one or more properties of a substrate, and in particular, how one or more properties of different substrates or different layers of the same substrate vary from layer to layer and/or across a substrate. The inspection apparatus may be integrated into the lithographic apparatus LA or the lithocell LC or may be a stand-alone device. To enable most rapid measurements, it is desirable that the inspection apparatus measure one or more properties in the exposed resist layer immediately after the exposure. However, the latent image in the resist has a very low contrast—there is only a very small difference in refractive index between the part of the resist which has been exposed to radiation and that which has not—and not all inspection apparatus have sufficient sensitivity to make useful measurements of the latent image. Therefore measurements may be taken after the post-exposure bake step (PEB) which is customarily the first step carried out on an exposed substrate and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibility for rework of a faulty substrate but may still provide useful information, e.g. for the purpose of process control.

A target used by a conventional scatterometer comprises a relatively large periodic structure layout (e.g., comprising one or more gratings), e.g., 40 µm by 40 µm. In that case, the measurement beam often has a spot size that is smaller than the periodic structure layout (i.e., the layout is underfilled such that one or more of the periodic structures is not completely covered by the spot). This simplifies mathematical reconstruction of the target as it can be regarded as infinite. However, for example, so the target can be positioned in among product features, rather than in the scribe lane, the size of a target has been reduced, e.g., to 20 µm by 20 µm or less, or to 10 µm by 10 µm or less. In this situation, the periodic structure layout may be made smaller than the measurement spot (i.e., the periodic structure layout is overfilled). Typically such a target is measured using dark field scatterometry in which the zeroth order of diffraction (corresponding to a specular reflection) is blocked, and only higher orders processed. Examples of dark field metrology can be found in PCT patent application publication nos. WO 2009/078708 and WO 2009/106279, which are hereby incorporated in their entirety by reference. Further developments of the technique have been described in U.S. patent application publications US2011-0027704, US2011-0043791 and US2012-0242970, which are hereby incorporated in their entirety by reference. Diffraction-based overlay using dark-field detection of the diffraction orders enables overlay measurements on smaller targets. These targets can be smaller than the illumination spot and may be surrounded by product structures on a substrate. In an embodiment, multiple targets can be measured in one image.

In an embodiment, the target on a substrate may comprise one or more 1-D periodic structures (e.g., gratings), which are printed such that after development, the bars are formed of solid resist lines. In an embodiment, the target may comprise one or more 2-D periodic periodic structures (e.g., gratings), which are printed such that after development, the one or more periodic structures are formed of solid resist pillars or vias in the resist. The bars, pillars or vias may alternatively be etched into the substrate. The pattern of the periodic structure is sensitive to chromatic aberrations in the lithographic projection apparatus, particularly the projection system PL, and illumination symmetry and the presence of such aberrations will manifest themselves in a variation in the printed periodic structure. Accordingly, the measured data of the printed periodic structures can be used to reconstruct the periodic structures. The parameters of the 1-D periodic structures, such as feature widths and shapes, or parameters of the 2-D structures, such as pillar or via widths or lengths or shapes, may be input to the reconstruction process, performed by processing unit PU, from knowledge of the printing step and/or other measurement processes.

A dark field metrology apparatus suitable for use in an embodiment is shown in FIG. 3(a). A target T (comprising a periodic structure such as a grating) and diffracted rays are illustrated in more detail in FIG. 3(b). The dark field metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, radiation emitted by an output 11 (e.g., a source such as a laser or a xenon lamp or an opening connected to a source) is directed onto substrate W via a prism 15 by an optical system comprising lenses 12, 14 and objective lens 16. These lenses are arranged in a double sequence of a 4F arrangement. A different lens arrangement can be used, provided that it still provides a substrate image onto a detector.

In an embodiment, the lens arrangement allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done, for example, by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis illumination from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary radiation outside the desired illumination mode may interfere with the desired measurement signals.

As shown in FIG. 3(b), target T is placed with substrate W substantially normal to the optical axis O of objective lens 16. A ray of illumination I impinging on target T from an angle off the axis O gives rise to a zeroth order ray (solid line 0) and two first order rays (dot-chain line +1 and double dot-chain line −1). With an overfilled small target T, these rays are just one of many parallel rays covering the area of the substrate including metrology target T and other features. Since the aperture in plate 13 has a finite width (necessary to admit a useful quantity of radiation), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the periodic structure pitch and illumination angle can be designed or adjusted so that the first order rays entering the objective lens are closely aligned with the central optical axis. The rays illustrated in FIGS. 3(a) and 3(b) are shown somewhat off axis, purely to enable them to be more easily distinguished in the diagram.

At least the 0 and +1 orders diffracted by the target on substrate W are collected by objective lens 16 and directed back through prism 15. Returning to FIG. 3(a), both the first and second illumination modes are illustrated, by designating diametrically opposite apertures labeled as north (N) and south (S). When the incident ray I is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled 1(S)) are the ones which enter the lens 16. Thus, in an embodiment, measurement results are obtained by measuring the target twice under certain conditions, e.g., after rotating the target or changing the illumination mode or changing the imaging mode to obtain separately the −1st and the +1st diffraction order intensities. Comparing these intensities for a given target provides a measurement of asymmetry in the target, and asymmetry in the target can be used as an indicator of a parameter of a lithography process, e.g., overlay error. In the situation described above, the illumination mode is changed.

A beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can also be used for many measurement purposes such as reconstruction, which are not described in detail here.

In the second measurement branch, optical system 20, 22 forms an image of the target on the substrate W on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image DF of the target formed on sensor 23 is formed from the −1 or +1 first order beam. The images captured by sensors 19 and 23 are output to image processor and controller PU, the function of which will depend on the particular type of measurements being performed. Note that the term 'image' is used here in a broad sense. An image of the periodic structure features (e.g., grating lines) as such will not be formed, if only one of the −1 and +1 orders is present.

The particular forms of aperture plate 13 and stop 21 shown in FIG. 3 are purely examples. In another embodiment, on-axis illumination of the targets is used and an aperture stop with an off-axis aperture is used to pass substantially only one first order of diffracted radiation to the sensor. In yet other embodiments, 2nd, 3rd and higher order beams (not shown in FIG. 3) can be used in measurements, instead of or in addition to the first order beams.

In order to make the illumination adaptable to these different types of measurement, the aperture plate 13 may comprise a number of aperture patterns formed around a disc, which rotates to bring a desired pattern into place, Note that aperture plate 13N or 13S are used to measure a periodic structure of a target oriented in one direction (X or Y depending on the set-up). For measurement of an orthogonal periodic structure, rotation of the target through 90° and 270° might be implemented. Different aperture plates are shown in FIGS. 3(c) and (d). FIG. 3(c) illustrates two further types of off-axis illumination mode. In a first illumination mode of FIG. 3(c), aperture plate 13E provides off-axis illumination from a direction designated, for the sake of description only, as 'east' relative to the 'north' previously described. In a second illumination mode of FIG. 3(c), aperture plate 13W is used to provide similar illumination, but from an opposite direction, labeled 'west'. FIG. 3(d) illustrates two further types of off-axis illumination mode. In a first illumination mode of FIG. 3(d), aperture plate 13NW provides off-axis illumination from the directions designated 'north' and 'west' as previously described. In a second illumination mode, aperture plate 13SE is used to provide similar illumination, but from an opposite direction, labeled 'south' and 'east' as previously described. The use of these, and numerous other variations and applications of the apparatus are described in, for example, the prior published patent application publications mentioned above.

FIG. 4 depicts an example composite metrology target formed on a substrate. The composite target comprises four periodic structures (in this case, gratings) 32, 33, 34, 35 positioned closely together. In an embodiment, the periodic structures are positioned closely together enough so that they all are within a measurement spot 31 formed by the illumination beam of the metrology apparatus. In that case, the four periodic structures thus are all simultaneously illuminated and simultaneously imaged on sensors 19 and 23. In an example dedicated to overlay measurement, periodic structures 32, 33, 34, 35 are themselves composite periodic structures (e,g., composite gratings) formed by overlying periodic structures, i.e., periodic structures are patterned in different layers of the device formed on substrate W and such that at least one periodic structure in one layer overlays at least one periodic structure in a different layer. Such a target may have outer dimensions within 20 μm×20 μm or within 16 μm×16 μm. Further, all the periodic structures are used to measure overlay between a particular pair of layers. To facilitate a target being able to measure more than a single pair of layers, periodic structures 32, 33, 34, 35 may have differently biased overlay offsets in order to facilitate measurement of overlay between different layers in which the different parts of the composite periodic structures are formed. Thus, all the periodic structures for the target on the substrate would be used to measure one pair of layers and all the periodic structures for another same target on the substrate would be used to measure another pair of layers, wherein the different bias facilitates distinguishing between the layer pairs. The meaning of overlay bias will be explained below, particularly with reference to FIG. 7.

FIGS. 7(a)-(c) show schematic cross sections of overlay periodic structures (in this case gratings) of respective targets T, with different biases. These can be used on substrate W, as seen in FIGS. 3 and 4. Periodic structures with periodicity in the X direction are shown for the sake of example only. Different combinations of these periodic structures with different biases and with different orientations can be provided.

Starting with FIG. 7(a), a composite overlay target 600 formed in two layers, labeled L1 and L2, is depicted. In the bottom layer L1, a first periodic structure (in this case a grating) is formed by features (e.g., lines) 602 and spaces 604 on a substrate 606. In layer L2, a second periodic structure (in this case a grating) is formed by features (e.g., lines) 608 and spaces 610. (The cross-section is drawn such that the features 602, 608 extend into the page.) The periodic structure pattern repeats with a pitch P in both layers. Lines 602 and 608 are mentioned for the sake of example only, other types of features such as dots, blocks and via holes can be used. In the situation shown at FIG. 7(a), there is no overlay error and no bias, so that each feature 608 lies exactly over a feature 602 in the bottom periodic structure (where the measurement is "line-on-line"—in an embodiment, no overlay error may occur where each feature 608 lies exactly over a space 610 wherein the measurement is "line-on-trench").

At FIG. 7(b), the same target with a bias +d is depicted such that the features 608 of the upper periodic structure are shifted by a distance d to the right (the distance d being less than the pitch P), relative to the features 602 of the lower periodic structures. That is, features 608 and features 602 are arranged so that if they were both printed exactly at their nominal locations, features 608 would be offset relative to the features 602 by the distance d. The bias distance d might be a few nanometers in practice, for example 10 nm 20 nm, while the pitch P is for example in the range 300-1000 nm, for example 500 nm or 600 nm. At FIG. 7(c), the same target with a bias −d is depicted such that the features 608 are shifted to the left relative to the features 602. Biased targets of this type shown at FIGS. 7(a) to (c), and their use in measurement, are described in, for example, the patent application publications mentioned above.

Further, as alluded to above, while FIGS. 7(a)-(c) depicts the features 608 lying over the features 602 (with or without a small bias of +d or −d applied), which is referred to as a "line on line" target having a bias in the region of zero, a target may have a programmed bias of P/2, that is half the pitch, such that each feature 608 in the upper periodic structure lies over a space 604 in the lower periodic structure. This is referred to as a "line on trench" target. In this case, a small bias of +d or −d may also be applied. The choice between "line on line" target or a "line on trench" target depends on the application.

Returning to FIG. 4, periodic structures 32, 33, 34, 35 may also differ in their orientation, as shown, so as to diffract incoming radiation in X and Y directions. In one example, periodic structures 32 and 34 are X-direction periodic structures with biases of +d, −d, respectively. Periodic structures 33 and 35 may be Y-direction periodic structures with offsets +d and −d respectively. While four periodic structures are illustrated, another embodiment may include a larger matrix to obtain desired accuracy. For example, a 3×3 array of nine composite periodic structures may have biases −4d, −3d, −2d, −d, 0, +d, +2d, +3d, +4d. Separate images of these periodic structures can be identified in the image captured by sensor 23.

FIG. 5 shows an example of an image that may be formed on and detected by the sensor 23, using the target of FIG. 4 in the apparatus of FIG. 3, using the aperture plates 13NW or 13SE from FIG. 3(d). While the sensor 19 cannot resolve the different individual periodic structures 32 to 35, the sensor 23 can do so. The dark rectangle represents the field of the image on the sensor, within which the illuminated spot 31 on the substrate is imaged into a corresponding circular area 41. Within this, rectangular areas 42-45 represent the images of the periodic structures 32 to 35. If the periodic structures are located in product areas, product features may also be visible in the periphery of this image field. Image processor and controller PU processes these images using pattern recognition to identify the separate images 42 to 45 of periodic structures 32 to 35. In this way, the images do not have to be aligned very precisely at a specific location within the sensor frame, which greatly improves throughput of the measuring apparatus as a whole.

Once the separate images of the periodic structures have been identified, the intensities of those individual images can be measured, e.g., by averaging or summing selected pixel intensity values within the identified areas. Intensities and/or other properties of the images can be compared with one another. These results can be combined to measure different parameters of the lithographic process. Overlay performance is an example of such a parameter.

FIG. 6 illustrates how, using for example the method described in PCT patent application publication no. WO 2011/012624, overlay error between the two layers containing the component periodic structures 32 to 35 is measured through asymmetry of the periodic structures, as revealed by comparing their intensities in the +1 order and −1 order dark field images. At step M1, the substrate, for example a semiconductor wafer, is processed through the lithographic cell of FIG. 2 one or more times, to create a structure including the target comprising periodic structures 32-35. At M2, using the metrology apparatus of FIG. 3, an image of the periodic structures 32 to 35 is obtained using one of the first order diffracted beams (say −1). In an embodiment, a first illumination mode (e.g., the illumination mode created using aperture plate 13NW) is used. Then, whether by, for example, changing the illumination mode, or changing the imaging mode, or by rotating substrate W by 180° in the field of view of the metrology apparatus, a second image of the periodic structures using the other first order diffracted beam (+1) can be obtained (step M3). Consequently, the +1 diffracted radiation is captured in the second image. In an embodiment, the illuminated mode is changed and a second illumination mode (e.g., the illumination mode created using aperture plate 13SE) is used. In an embodiment, tool-induced artifacts like TIS (Tool Induced Shift) can be removed by doing the measurement at 0° and 180° substrate orientation.

Note that, by including only half of the first order diffracted radiation in each image, the 'images' referred to here are not conventional dark field microscopy images. The individual periodic structure features are not resolved. Each periodic structure will be represented simply by an area of a certain intensity level. In step M4, a region of interest (ROI) is identified within the image of each component periodic structure, from which intensity levels will be measured.

Having identified the region of interest P1, P2, P3, P4 for each respective individual periodic structure 32-35 and measured its intensity, the asymmetry of the periodic structure, and hence, e.g., overlay error, can then be determined. This is done by the image processor and controller PU in step M5 comparing the intensity values obtained for +1 and −1 orders for each periodic structure 32-35 to identify any difference in their intensity, i.e., an asymmetry. The term "difference" is not intended to refer only to subtraction. Differences may be calculated in ratio form. In step M6 the measured asymmetries for a number of periodic structures are used together with, if applicable, knowledge of the overlay biases of those periodic structures to calculate one or more performance parameters of the lithographic process in the vicinity of the target T. A performance parameter of interest is overlay. Other parameters of performance of the lithographic process can be calculated such as focus and/or dose. The one or more performance parameters can be fed back for improvement of the lithographic process, used to improve the measurement and calculation process of FIG. 6 itself, used to improve the design of the target T, etc.

Figure 8:
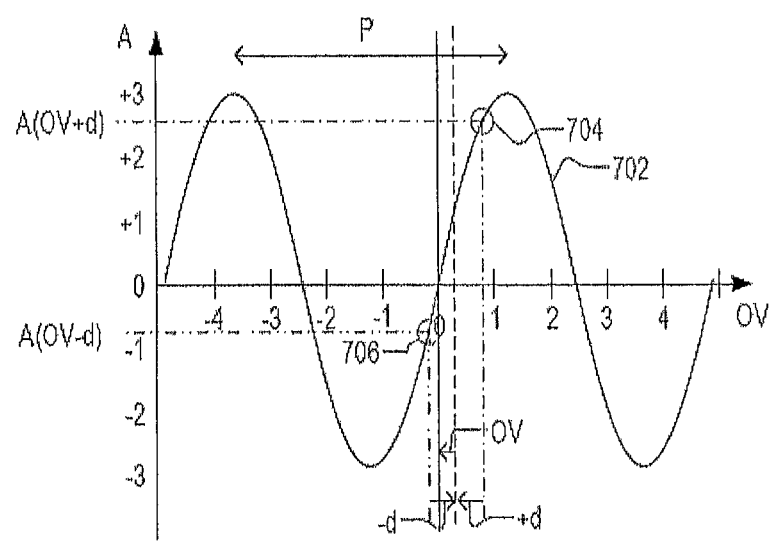
FIG. 8 illustrates principles of overlay measurement in an ideal target structure.

In an embodiment to determine overlay, FIG. 8 depicts a curve 702 that illustrates the relationship between overlay error OV and measured asymmetry A for an 'ideal' target having zero offset and no structural asymmetry within the individual periodic structures forming the overlay target. These graphs are to illustrate the principles of determining the overlay only, and in each graph, the units of measured asymmetry A and overlay error OV are arbitrary.

In the 'ideal' situation of FIGS. 7(a)-(c), the curve 702 indicates that the measured asymmetry A has a sinusoidal relationship with the overlay. The period P of the sinusoidal variation corresponds to the period (pitch) of the periodic structures, converted of course to an appropriate scale. The sinusoidal form is pure in this example, but can include harmonics in real circumstances. For the sake of simplicity, it is assumed in this example (a) that only first order diffracted radiation from the target reaches the image sensor 23 (or its equivalent in a given embodiment), and (b) that the experimental target design is such that within these first orders a pure sine-relation exists between intensity and overlay between upper and lower periodic structures results. Whether this is true in practice is a function of the optical system design, the wavelength of the illuminating radiation and the pitch P of the periodic structure, and the design and stack of the target.

As mentioned above, biased periodic structures can be used to measure overlay, rather than relying on a single measurement. This bias has a known value defined in the patterning device (e.g. a reticle) from which it was made, that serves as an on-substrate calibration of the overlay corresponding to the measured signal. In the drawing, the calculation is illustrated graphically. In steps M1-M5 of FIG. 6, asymmetry measurements A(+d) and A(−d) are obtained for component periodic structures having biases +d an −d respectively (as shown in FIGS. 7(b) and 7(c), for example). Fitting these measurements to the sinusoidal curve gives points 704 and 706 as shown. Knowing the biases, the true overlay error OV can be calculated. The pitch P of the sinusoidal curve is known from the design of the target. The vertical scale of the curve 702 is not known to start with, but is an unknown factor which we can call a 1st harmonic proportionality constant, K.

In equation terms, the relationship between overlay and measured asymmetry A is assumed to be:

$$A = K \sin(OV)$$

where OV is expressed on a scale such that the periodic structure pitch P corresponds to an angle 2π radians. Using two measurements with periodic structures with different, known biases to arrive at two values of A, one can solve two equations to calculate the unknowns K and overlay OV.

Although these measurement techniques are fast and relatively computationally simple (once calibrated), they rely on an assumption that the overlay/lateral shift is the only cause of asymmetry. That is, it assumes an 'ideal' situation with, for example, no structural asymmetry in the target. Any structural asymmetry in the stack, such as asymmetry of features within one or both of the overlaid periodic structures, also causes an asymmetry in the 1st orders besides the overlay/lateral shift. This structural asymmetry which is not related to the overlay clearly perturbs the measurement, giving an inaccurate result.

As an example of structural asymmetry, one or more of the periodic structures of the target may be structurally deformed. For example, one or more side walls of periodic structure features (e.g., grating lines) of the target may not be vertical as intended. As another example, one or spaces between periodic structure features (e.g., grating spaces or trenches) of a target may be larger or smaller than as intended. Further, one or more features of a periodic structure of a target (e.g., grating lines) may have a smaller or larger width than as intended. Additionally, even where a difference from intended is uniform for one or more periodic structures of the target, that difference from intended may not be the same as for one or more other periodic structures of the target. Structural asymmetry in the lower periodic structure of a composite target is a common form of structural asymmetry. It may originate, for example, in the substrate processing steps such as chemical-mechanical polishing (CMP), performed after the lower periodic structure was originally formed.

Referring to FIG. 7(d), an example of structural asymmetry of a lower periodic structure is schematically depicted. The features and spaces in the periodic structures at FIGS. 7(a) to (c) are shown as perfectly square-sided, when a real feature and space would have some slope on a surface, and a certain roughness. Nevertheless they are intended to be at least symmetrical in profile. The features 602 and/or spaces 604 at FIG. 7(d) in the lower periodic structure no longer have a symmetrical form at all, but rather have become distorted by, for example, one or more processing steps. Thus, for example, a bottom surface of each space 604 has become tilted. Side wall angles of the features and spaces have become asymmetrical also. When overlay is measured by the method of FIG. 6 using only two biased periodic structures, the structural asymmetry cannot be distinguished from overlay, and overlay measurements become unreliable as a result.

Thus, accuracy in measurement (e.g., measurement of alignment where the target is used for alignment, measurement of overlay where the target is used for overlay measurement, etc.) can be significantly reduced by asymmetric structural deformation of one or more periodic structures (e.g., gratings) of the target.

An embodiment will be described in terms of +1st and −1st order diffraction-based measurement of a diffraction target used to measure overlay. Some of the principles of such a measurement technique have been described above. An embodiment, however, may apply to other measurement techniques using a target. For example, the techniques described herein may be applied to measurement of an alignment target.

Figure 9:
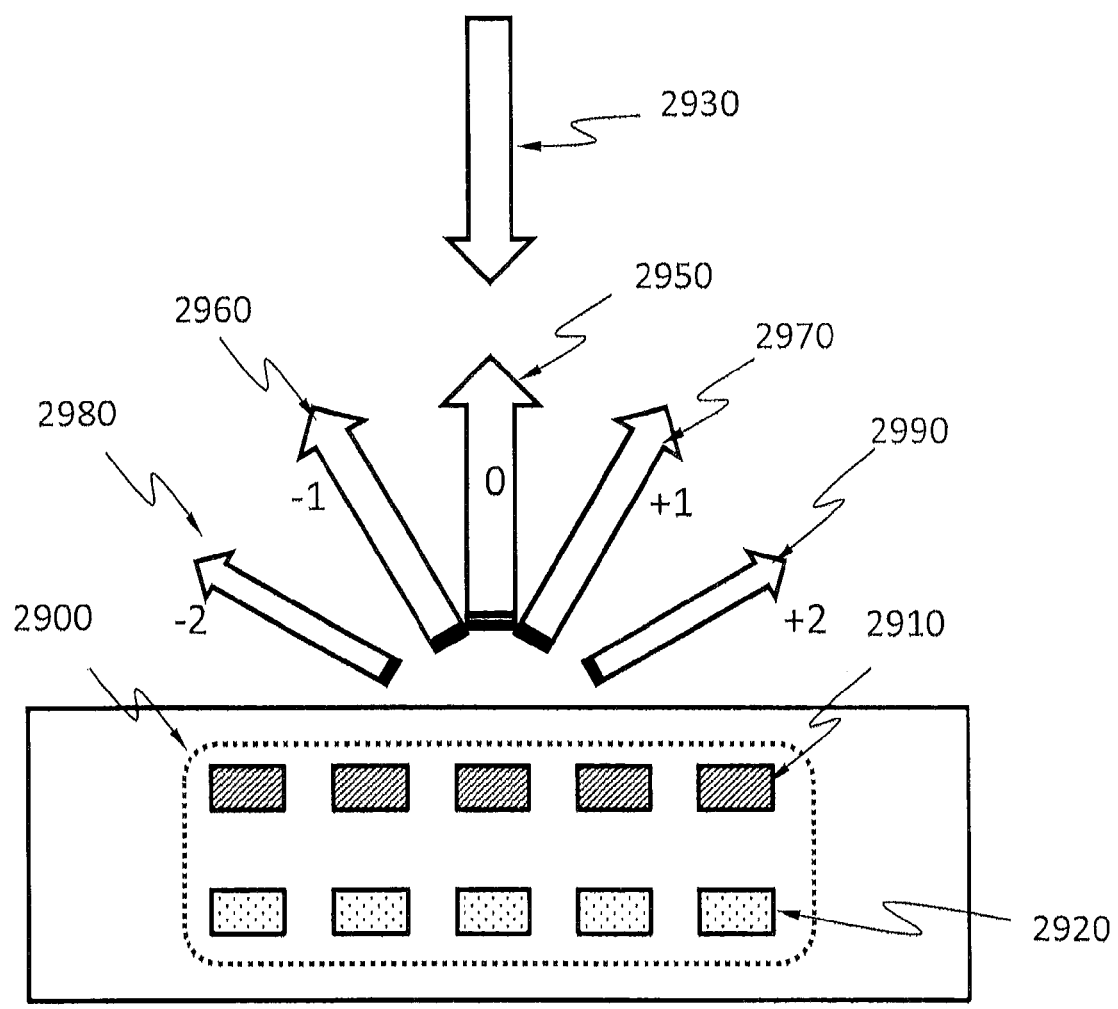
FIG. 9 schematically shows that alignment between patterns on different layers affects the diffraction.

Thus, as discussed above, measurement of Measurement of overlay error using, for example, scatterometry may use, among other things, radiation diffracted from a target structure. FIG. 9 schematically shows diffraction of incident radiation 2930 from a target structure 2900. The target structure 2900 has a plurality (e.g., two) of periodic structures (e.g., gratings) 2910 and 2920 in different layers. The diffraction may have multiple diffraction orders, such as the zeroth order 2950, the $-1^{st}$ order 2960, the $+1^{st}$ order 2970, the $-2^{nd}$ order 2980 and the $+2^{nd}$ order 2990, etc. One or more characteristics (e.g., intensity and/or direction) of the diffraction orders are affected by the one or more characteristics (e.g., wavelength, incident angle, polarization, etc.) of incident radiation 2930 and one or more characteristics of the target structure 2900. In this particular example, the characteristics of the target structure that affect the intensity and direction of the diffraction orders may include the periodicity, depth, and alignment of the periodic structures 2910 and 2920, One way to characterize the overlay error is by using characteristics of the diffraction orders, such as the difference between the −m-th order and the +m-th diffraction order. Using the $+1^{st}$ and $-1^{st}$ diffraction orders as an example, the overlay error may be expressed as $$OV = f(I_{+1} - I_{-1})$$

where OV is the overlay error (e.g., in the form of a distance of misalignment between the periodic structures 2910 and 2920), $I_{+1}$ is the peak intensity of the $+1^{st}$ diffraction order, and $I_{-1}$ is the peak intensity of the $-1^{st}$ diffraction order. The overlay error may be characterized using other characteristics of the diffraction, for example more than one differences among diffraction orders. More broadly speaking, the overlay error may be expressed as $$OV = f(\ldots, I_{-2}, I_{-1}, I_0, I_{+1}, I_{+2}, \ldots).$$

Figure 10:
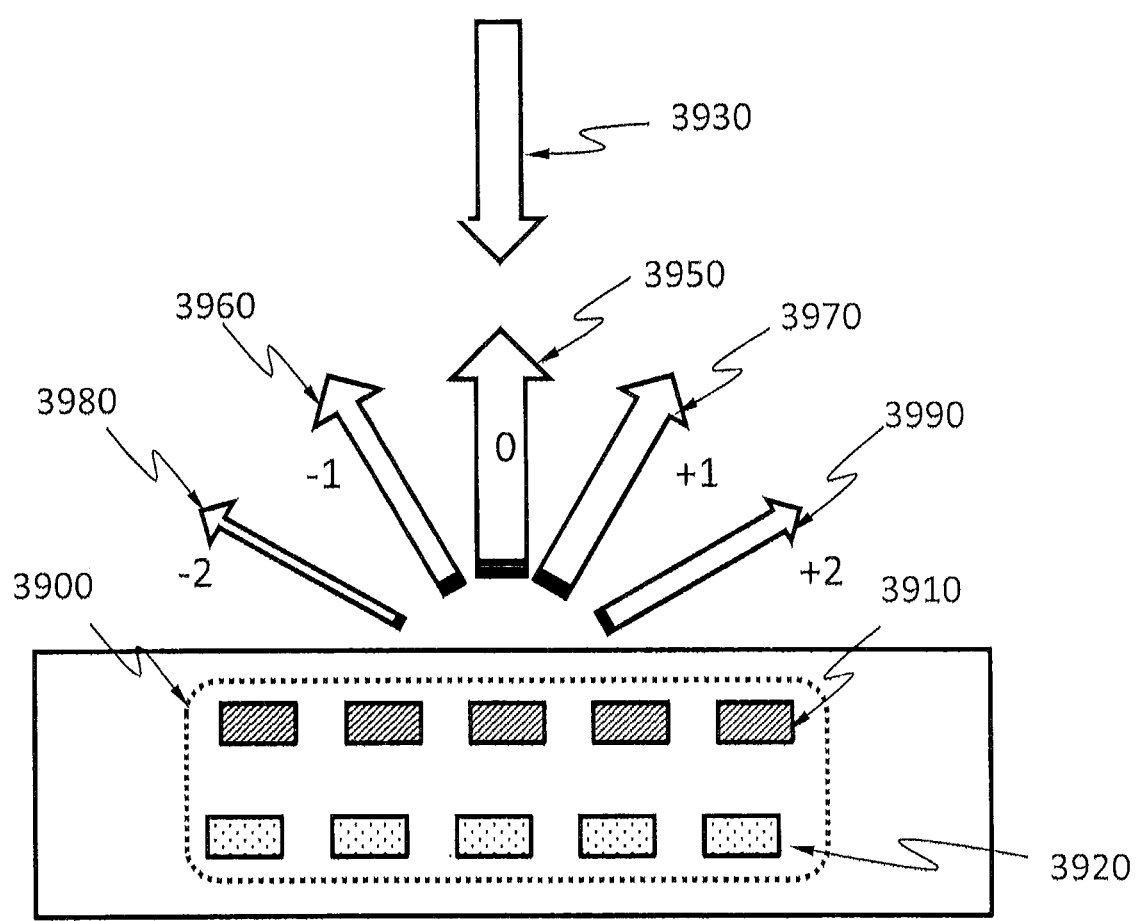
FIG. 10 schematically shows that misalignment between patterns on different layers affects the diffraction.

FIG. 10 schematically shows that alignment or misalignment between patterns on different layers affects the diffraction. Incident radiation 3930 diffracts from a target structure 3900, which has two periodic structures 3910 and 3920 in different layers. The incident radiation 3930 and the two periodic structures 3910 and 3920 can be the same as those in FIG. 9 except that the two periodic structures 3910 and 3920 are misaligned. The diffraction from the target structure 3900 may also have multiple diffraction orders, such as the zeroth order 3950, the $-1^{st}$ order 3960, the $+1^{st}$ order 3970, the $-2^{nd}$ order 3980 and the $+2^{nd}$ order 3990, etc. The misalignment may manifest itself in the imbalance of the intensities of the −m-th order and the +m-th order. For example, as schematically represented by different thickness, the $+1^{st}$ order may have a higher intensity than the $-1^{st}$ order and/or the $+2^{nd}$ order may have a higher intensity than the $-2^{nd}$ order.

The relationship between the imbalance of the −m-th order and the +m-th order and the overlay error may be calibrated by curve fitting the measured values of the overlay error at one or more known values of misalignment to characteristics of the diffraction orders (e.g., imbalance of the −m-th order and the +m-th order) at these known values of misalignment. For example, the two periodic structures 3910 and 3920 can be offset from each other by $\vec{d}_k$ and the values of the overlay error at the offsets of $\vec{d}_k$ are fitted against the imbalance of the $+1^{st}$-order and the $-1^{st}$-order at the offsets of $\vec{d}_k$. The overlay error may depend linearly from $(I_{+1}-I_{-1})$.

Figure 11:
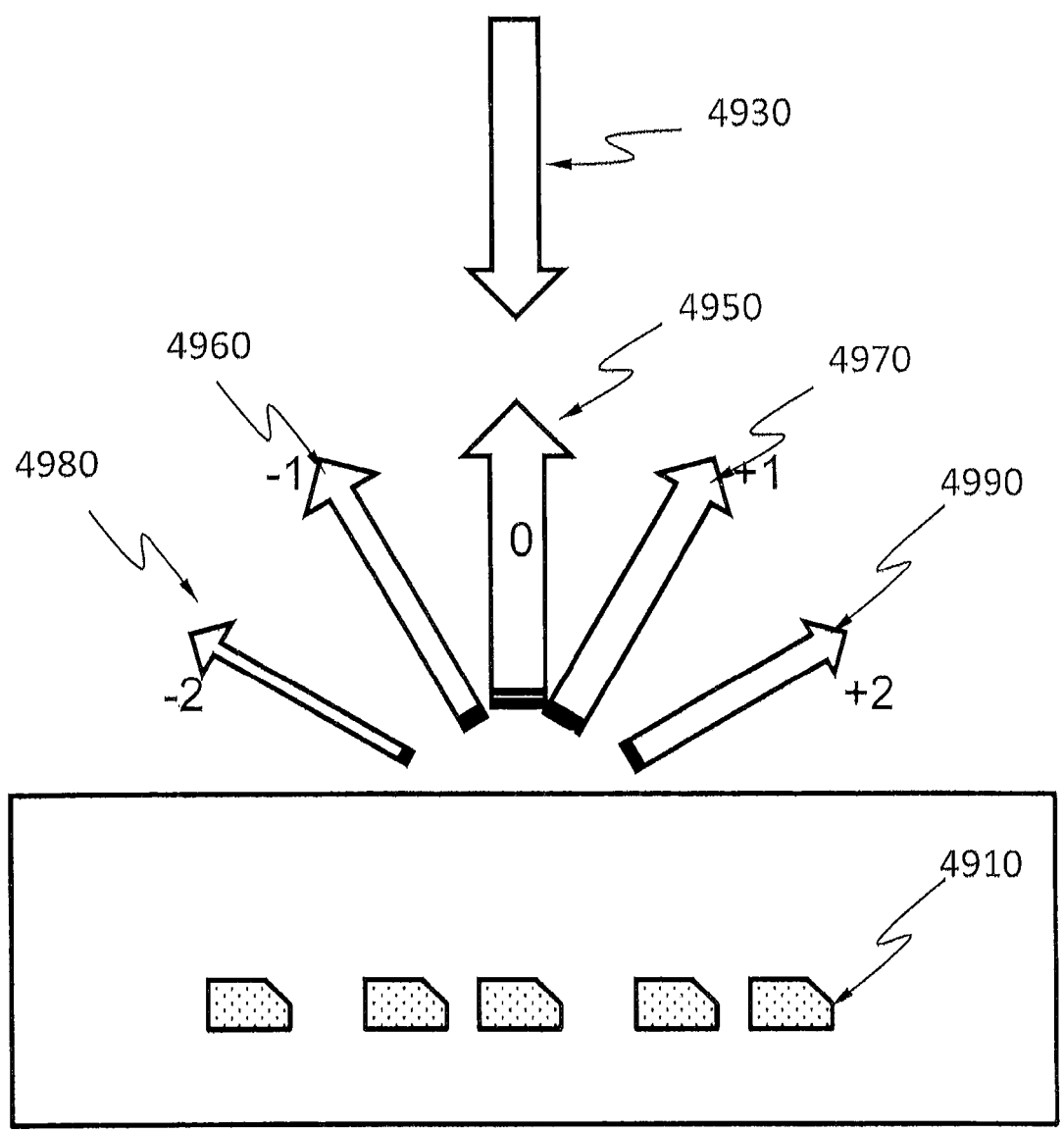
FIG. 11 schematically shows an example where a single periodic structure leads to imbalance between the −m-th order and the +m-th order.

However, as noted above, the characteristics of the diffraction are not only affected by misalignment of patterns on different layers. If the other factors that affect the characteristics of the diffraction are not taken into account when determining the overlay error from the characteristics of the diffraction, a systematic error caused by the other factors may occur. FIG. 11 schematically shows an example where a single periodic structure leads to imbalance between the −m-th order and the +m-th order. Incident radiation 4930 diffracts from a target structure 4910, which is a single periodic structure that is asymmetric, does not have a single period, or both. The diffraction from the target structure 4910 may still have multiple diffraction orders, such as the zeroth order 4950, the $-1^{st}$ order 4960, the $+1^{st}$ order 4970, the $-2^{nd}$ order 4980 and the $+2^{nd}$ order 4990, etc., but the −m-th order and the +m-th order may have imbalance (e.g., having different intensity, direction, or both), even without the presence of a second periodic structure or any misalignment from a second periodic structure. The periodic structure that is asymmetric, does not have a single period, or both, is not uncommon. For example, a periodic structure may be asymmetric because one or more sidewalls of one or more features that constitute the periodic structure may have a different sidewall angle than another feature that constitutes the periodic structure. For example, a periodic structure may not have a single period because the features that constitute the periodic structure may shift relative to one another.

With one or more systematic errors removed, the overlay error may be generally expressed as $$OV=f_{apparent}(\ldots, I_{-2}, I_{-1}, I_0, I_{+1}, I_{+2}, \ldots)-f_{error}.$$

$f_{error}$ is the systematic error and $f_{apparent}$ is the apparent overlay error. The term "apparent overlay error" as used herein means an overlay error determined from one or more apparent characteristics (e.g., peak intensities, directions or both) of diffraction orders. The term "apparent characteristic" as used herein means a characteristic (e.g., peak intensity, direction) of a diffraction order with contribution of at least one factor other than misalignment of patterns on different layers.

Figure 12:
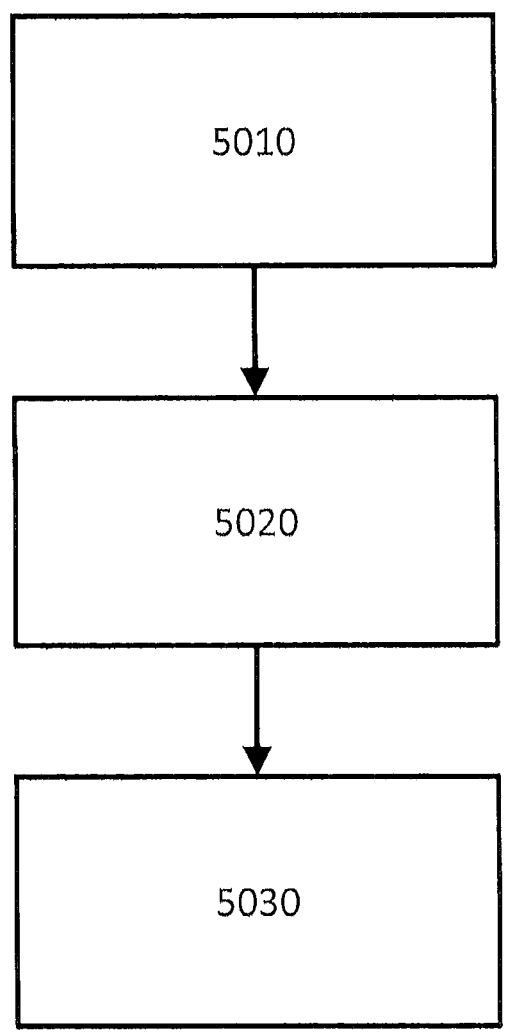
FIG. 12 shows a flow chart of a method for determining an overlay error.

FIG. 12 shows a flow chart of a method for determining an overlay error. In step 5010, an apparent overlay error is determined. For example, the apparent overlay error may be interpolated or extrapolated from the curve fitted from the values of the measured overlay error (e.g., by a metrology tool such as scanning electron microscope (SEM)) to characteristics of the diffraction orders at one or more known values of misalignment to these known values of misalignment. In step 5020, a systematic error of overlay error is determined. The systematic error is an error in the apparent overlay error caused by one or more factors other than misalignment of patterns on different layers. The systematic error may be determined before or after the patterns on different layers are completely fabricated. For example, if the patterns include two patterns on two different layers, the systematic error may be determined after the pattern on the lower layer is fabricated but before the pattern on the upper layer is fabricated. Alternatively, the systematic error may be determined after both patterns are fabricated using the process depicted in FIG. 14 and FIG. 15A. In step 5030, an overlay error is determined by subtracting the systematic error from the apparent overlay error.

Alternatively, the systematic error may be removed by subtracting from the one or more apparent characteristics (e.g., peak intensity, direction or both) of diffraction orders . . . , $I_{-2}, I_{-1}, I_0, I_{+1}, I_{+2}, \ldots$ contributions of one or more factors other than misalignment of patterns on different layers. For example, the overlay error with the systematic error removed can also be expressed as OV=f( . . . , $I'_{-2}, I'_{-1}, I'_0, I'_{+1}, I'_{+2}, \ldots$) where . . . , $I'_{-2}, I'_{-1}, I'_0, I'_{+1}, I'_{+2}, \ldots$ are corrected peak intensities of the diffraction orders (i.e., peak intensities without contributions of one or more factors other than misalignment of patterns on different layers). The term "corrected characteristic" as used herein means a diffraction order characteristic (e.g., peak intensity, direction) without contribution of a factor other than misalignment of patterns on different layers.

Figure 13:
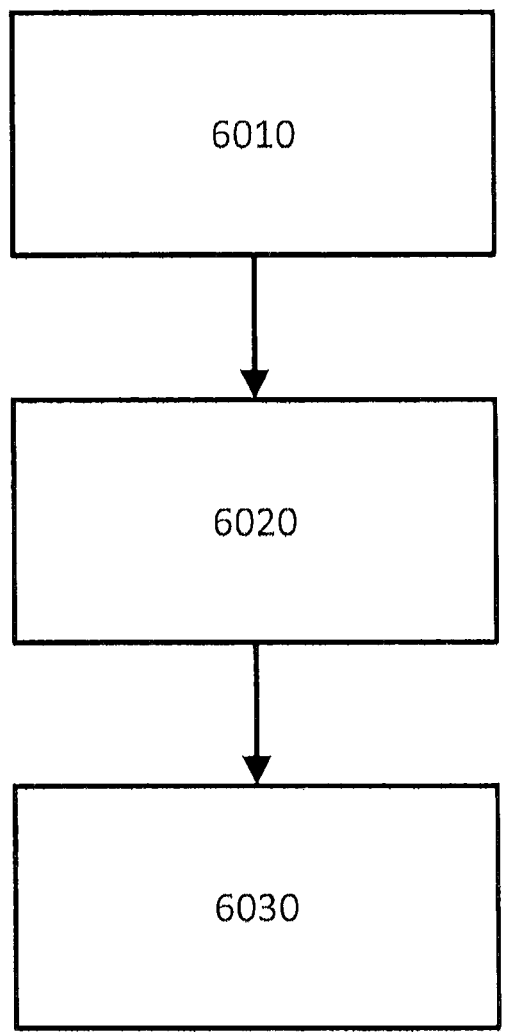
FIG. 13 shows a flow chart of a method for determining an overlay error.

FIG. 13 shows a flow chart of a method for determining an overlay error. In step 6010, one or more apparent characteristics (e.g., peak intensity, direction or both) of diffraction orders are determined. For example, the apparent characteristics of the diffraction orders may be determined by optically measuring a diffraction pattern. In step 6020, a corrected characteristic of the diffraction orders is determined. For example, a corrected characteristic may be determined by subtracting a contribution of a factor other than misalignment of patterns on different layers. The contribution may be physically measured, e.g., from patterns on each layer where they do not overlap with patterns on other layers, or calculated from patterns on each layer, e.g., by any suitable model such as Fourier transform of the patterns. The corrected characteristic may be determined before or after the patterns on different layers are completely fabricated. For example, if the patterns include two patterns on two different layers, the contribution of the pattern on the lower layer may be determined after the pattern on the lower layer is fabricated but before the pattern on the upper layer is fabricated. Alternatively, the corrected characteristic may be determined after both patterns are fabricated using the process depicted in FIG. 14 and FIG. 15B. In step 6030, an overlay error is determined from the corrected characteristic.

Figure 14:
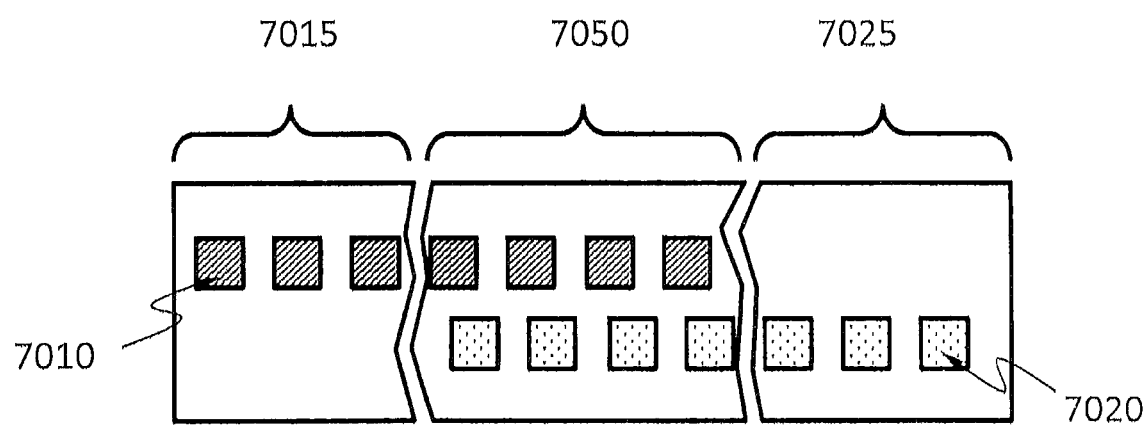
FIG. 14 shows a structure with partially overlapping periodic structures on different layers.

FIG. 14 shows a structure that can be used to determine the systematic error and the corrected characteristic. This structure may include two patterns (e.g., gratings) 7010 and 7020 on different layers. Only pattern 7010 but not pattern 7020 is in area 7015. Only pattern 7020 but not pattern 7010 is in area 7025. Both patterns 7010 and 7020 are in area 7050—patterns 7010 and 7020 overlap in area 7050. The areas 7015, 7025 and 7050 may be adjacent to one another. In an example, pattern 7010 in areas 7015 and 7050 may be in the form of a periodic structure (e.g., a grating) extending into both of these areas. In an example, pattern 7020 in areas 7025 and 7050 may be in the form of a periodic structure extending into both of these areas.

Figure 15A:
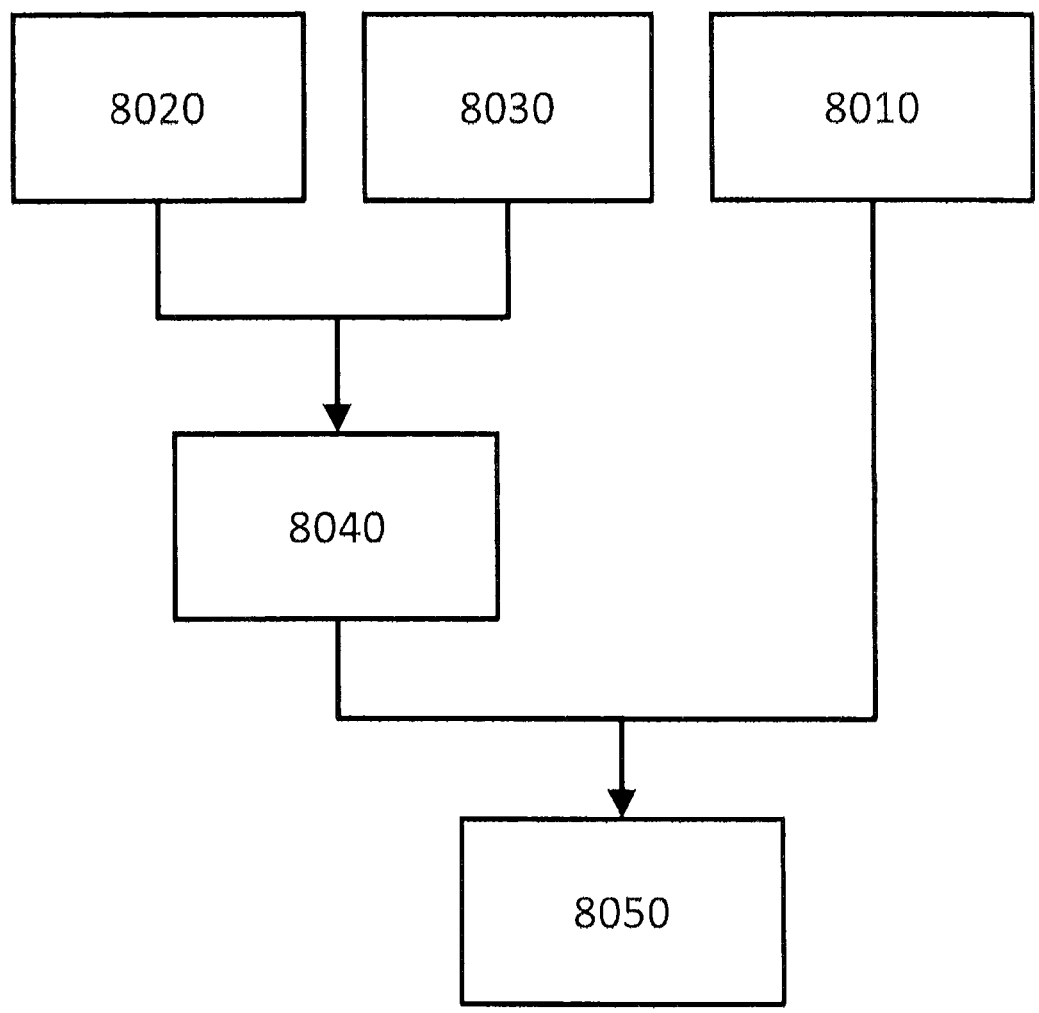
FIG. 15A shows a method of determining the systematic error using the structure of FIG. 14.

FIG. 15A shows a method of determining the systematic error using the structure of FIG. 14. In step 8010, one or more apparent characteristics of diffraction orders are measured in area 7050—where patterns 7010 and 7020 overlap. In step 8020, one or more characteristics of pattern 7010 are measured in area 7015—where pattern 7010 does not overlap pattern 7020. The one or more characteristics may be one or more characteristics of diffraction orders of pattern 7010 in area 7015, or one or more geometrical characteristics such as periodicity, shape, size, etc. of pattern 7010. In step 8030, one or more characteristics of pattern 7020 are measured in area 7025—where pattern 7020 does not overlap pattern 7010. The one or more characteristics may be one or more characteristics of diffraction orders of pattern 7020 in area 7025, or one or more geometrical characteristics such as periodicity, shape, size, etc. of pattern 7020. In step 8040, the systematic error of patterns 7010 and 7020 is determined at least from the one or more characteristics of pattern 7010 measured in area 7015 and the one or more characteristics of pattern 7020 measured in area 7025. In step 8050, the overlay error is determined using the systematic error.

Figure 15B:
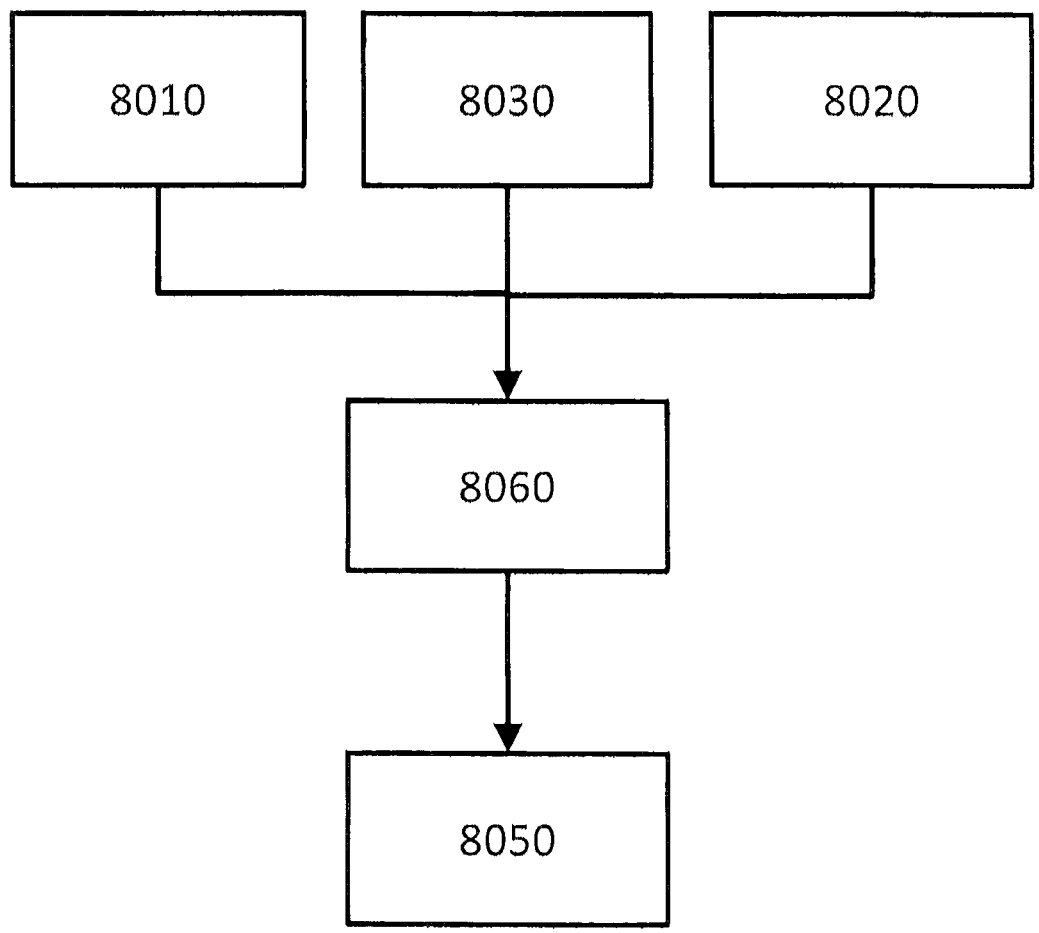
FIG. 15B shows a method of determining the corrected characteristics using the structure of FIG. 14.

FIG. 15B shows a method of determining the corrected characteristics using the structure of FIG. 14. In step 8010, one or more apparent characteristics of diffraction orders are measured in area 7050—where patterns 7010 and 7020 overlap. In step 8020, one or more characteristics of pattern 7010 are measured in area 7015—where pattern 7010 does not overlap pattern 7020. The one or more characteristics may be one or more characteristics of diffraction orders of pattern 7010 in area 7015, or one or more geometrical characteristics such as periodicity, shape, size, etc. of pattern 7010. In step 8030, one or more characteristics of pattern 7020 are measured in area 7025—where pattern 7020 does not overlap pattern 7010. The one or more characteristics may be one or more characteristics of diffraction orders of pattern 7020 in area 7025, or one or more geometrical characteristics such as periodicity, shape, size, etc. of pattern 7020. In step 8060, one or more corrected characteristics are determined at least from one or more characteristics of pattern 7010 measured in area 7015, one or more characteristics of pattern 7020 measured in area 7025, and one or more apparent characteristics of the diffraction orders measured in area 7050 where patterns 7010 and 7020 overlap. In step 8050, the overlay error is determined using the corrected characteristics.

So, when using bias, it is assumed that asymmetry gives the same error to the intensity reading independently of the bias. So the intensity $I_{+1}-I_{-1}=I_{+1}-I_{-1}+\Delta I$ in both periodic structures with +d and −d bias, where $\Delta I$ is the intensity asymmetry artifact induced by target deformation. Further, since etching is most likely to introduce asymmetry to the bottom structure and it is more difficult to correct, it is assumed that $\Delta t$ is introduced by the bottom periodic structure. Hence, overlay becomes: $OV_{measured}=OV_{real}+d[2\Delta I]/[(I_+-I_-)_{+d}-(I_+-I_-)_{-d}]$ where the second term is the equivalent overlay error induced by bottom periodic structure deformation and the denominator is composed of measured quantities independent of asymmetry artifact.

So, an embodiment of a method can include:

1. Measuring for the lower periodic structure(s), e.g., the periodic structure 7020 in the area 7025, the intensity and the intensity differences of the +1 and −1 orders on +d and −d target areas. This would yield a measured intensity asymmetry $\Delta I_{bottom}=[(N_+-N_-)_{+d}+(N_+-N_-)_{-d}]/2$, where N is used to denote the measured lower periodic intensities. Theoretically, $(N_+-N_-)_{+d}=(N_+-N_-)_{-d}$ can be expected. As discussed above, the lower periodic structure asymmetry measurements can be done as separate measurement steps on the same overlay target before and after printing the upper layer periodic structure (i.e., multiple metrology steps). Or, the lower periodic structure can be placed in the layer close to the overlay target (see FIG. 14). In this case, asymmetry measurements may be done in the same step as metrology overlay measurement. The measurement time may increase but would not require having an additional step in metrology inspection. In an embodiment, multiple targets can be measured simultaneously. In this case, bottom/top asymmetry measurements as well as overlay measurement can be done in the same step.

2. Alternatively or additionally, measuring for the upper layer periodic structure(s), e.g., the periodic structure 7010 in the area 7015, the intensity and the intensity differences of the +1 and −1 orders on +d and −d target areas. This would yield a measured intensity asymmetry $\Delta I_{top}=[(M_+-M_-)_{+d}+(M_+-M_-)_{-d}]/2$, where M is used to denote the measured top layer grating intensity. Theoretically, $(M_+-M_-)_{+d}=(M_+-M_-)_{-d}$ can be expected.

3. Measuring for an overlay target the overlay error including intensities and intensity asymmetries $(I_+-I_-)_{+d}$ and $(I_+-I_-)_{-d}$ on the same location, or close to the same location, of asymmetry measurement of the periodic structures.

4. With the measurement results of step 3, the apparent overlay value can be calculated as $OV=d[(I_+-I_-)_{+d}+(I_+-I_-)_{-d}]/[(I_+-I_-)_{+d}-(I_+-I_-)_{-d}]$.

5. Using the measurement results of steps 1 and/or 2, the equivalent overlay error caused by periodic structure asymmetry can be calculated: $S \cdot d[2\Delta I]/[(I_+-I_-)_{+d}-(I_+-I_-)_{-d}]$ where S is the scaling factor which can be determined computationally or through measurements (for example, as an intensity ratio between asymmetry and overlay measurements).

6. Using the results calculated in steps 4 and 5, the "true" overlay may be calculated. In other words the asymmetry caused by periodic structure deformation can be "corrected":
$OV_{true}=OV-S_{bottom} \cdot d[2\Delta I_{bottom}]/[(I_+-I_-)_{+d}-(I_+-I_-)_{-d}]$,
$OV_{true}=OV-S_{top} \cdot d[2\Delta I_{top}]/[(I_+-I_-)_{+d}-(I_+-I_-)_{-d}]$ or
$OV_{true}=OV-S_{bottom} \cdot d[2\Delta I_{bottom}]/[(I_+-I_-)_+-(I_+-I_-)_{-d}]-S_{top} \cdot d[2\Delta I_{top}]/[(I_+-I_-)_{+d}-(I_+-I_-)_{-d}]$ The results can be implemented in various ways. For example, in a feedforward approach, asymmetry measurements are used to calculate the error in the overlay metrology measurement. In that case, the denominator in the equation $OV_{measured}=OV_{real}+d[2\Delta I]/[(I_+-I_-)_{+d}-(I_+-I_-)_{-d}]$ is determined based on the overlay measurement of the full stack overlay target. The numerator is taken from asymmetry measurement of the targets, e.g., either after etching or after the full lithography layer stack is deposited. Then the asymmetry error on overlay is determined computationally. Even if different measurement recipes (e.g., wavelength, polarization, etc. of the measurement beam) are used for the two steps, this method may provide good scaling as the stack information is used to calculate the asymmetry effect on overlay. Further, signal distortion issue may be corrected by computation because the layer stack information is available. In this approach the lower layer asymmetry can be measured at any time of the process flow. Advantageously, no additional target design may be required and measurement can be carried out in the same locations as the target. But, additional measurement may delay the process cycle time and may be only capable of correcting lower layer asymmetry.

For example, in a feedback approach, matching pairs of periodic structures are created in the bottom and top layers (see, e.g., FIG. 14). Then separate measurements will be made. One on the fully developed overlay target as normal and additional measurements on the accompanying target with only the bottom and/or top layer periodic structure created (see, e.g., FIG. 14). The denominator and numerator of $OV_{measured} = OV_{real} + d[2\Delta I]/[(I_+ - I_-)_{+d} - (I_+ - I_-)_{-d}]$ can be acquired through the separate measurements and thus the "true overlay" can be derived using $OV_{true} = OV - S_{bottom} \cdot d[2\Delta I_{bottom}]/[(I_+ - I_-)_{+d} - (I_+ - I_-)_{-d}]$, $OV_{true} = OV - S_{top} \cdot d[2\Delta I_{top}]/[(I_+ - I_-)_{+d} - (I_+ - I_-)_{-d}]$ or $OV_{true} = OV - S_{bottom} \cdot d[2\Delta I_{bottom}]/[(I_+ - I_-)_{+d} - (I_+ - I_-)_{-d}] - S_{top} \cdot d[2\Delta I_{top}]/[(I_+ - I_-)_{+d} - (I_+ - I_-)_{-d}]$. Advantageously, this implementation may require no additional metrology step. Further, distortion of the lower layer asymmetry signal propagating through the upper layer is accounted for so that no additional treatment may be needed. This allows for correction of bottom layer asymmetry error. Similarly, distortion of the upper layer asymmetry signal is accounted for. This may allow for correcting for upper layer asymmetry error such as: ADI-AEI difference (top layer processing), metrology tool matching (additional measured asymmetry on ADI periodic structures), and aberration error (resist profile damaged due to aberrations). But, this implementation may require additional measurement and may require additional area for the accompanying target.

Figure 16A:
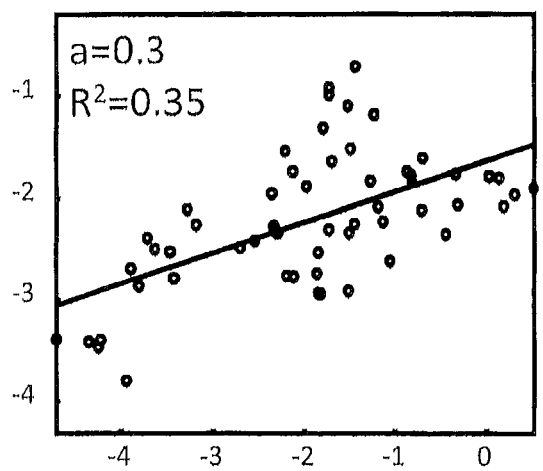
FIG. 16A shows a correlation of overlay errors patterns on different layers determined by a metrology tool (e.g., SEM) (vertical axis) and overlay errors of the same patterns determined using characteristics of diffraction orders (horizontal axis) without removing systematic errors or contributions of any factor other than misalignment of these patterns.
Figure 16B:
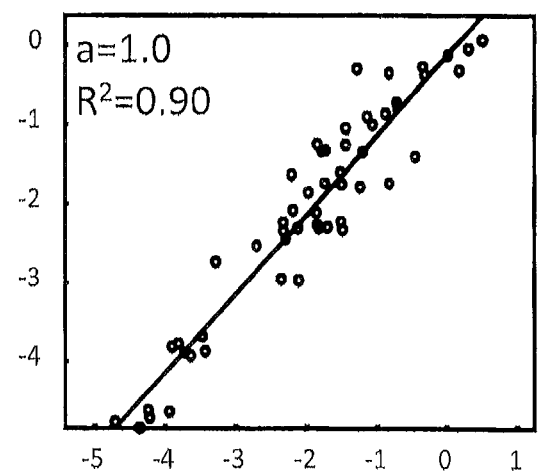
FIG. 16B show the same correlation as in FIG. 16A except that systematic errors or contributions of any factor other than misalignment of these patterns are removed.

FIG. 16A shows a correlation of overlay errors patterns on different layers determined by a metrology tool (e.g., SEM) (vertical axis) and overlay errors of the same patterns determined using one or more characteristics of diffraction orders (horizontal axis) without removing a systematic error or contribution of a factor other than misalignment of these patterns. FIG. 16B shows the same correlation as in FIG. 16A except that the systematic error or contribution of a factor other than misalignment of these patterns is removed. The fitting in FIG. 16B is much better than the fitting in FIG. 16A, as indicated by $R^2$ closer to one and slope closer to one. The contrast between FIG. 16A and FIG. 16B demonstrates that removing a systematic error or contribution of a factor other than misalignment of these patterns improves accuracy overlay error measurement using characteristics of diffraction orders.

Figure 17:
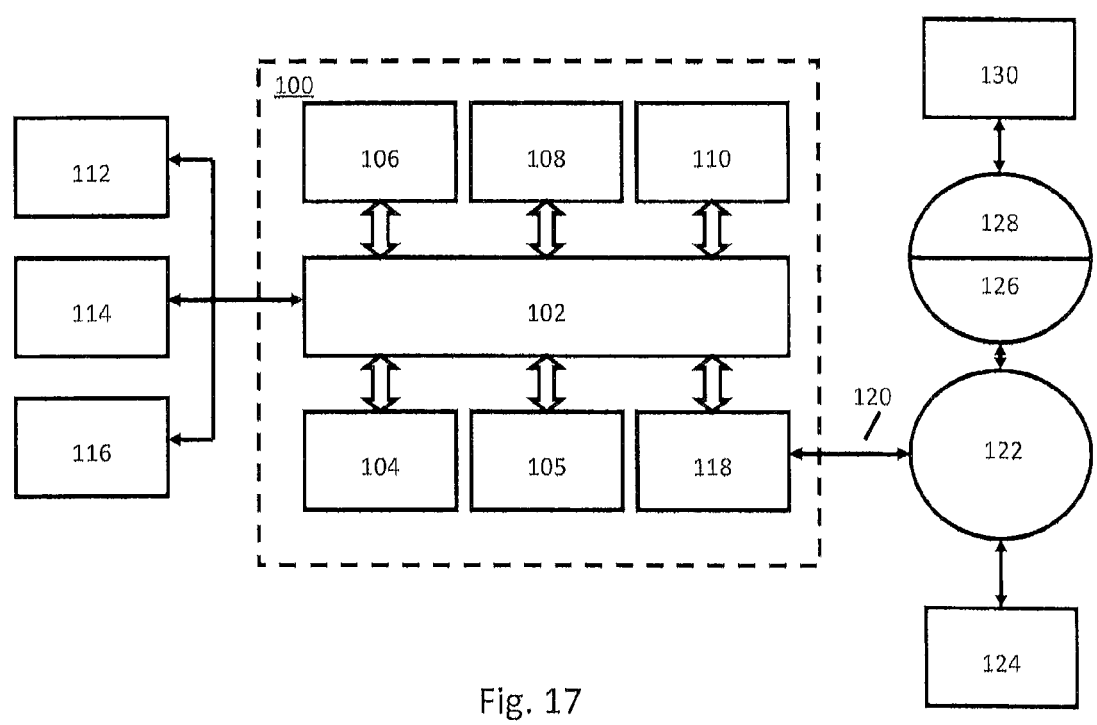
FIG. 17 is a block diagram of an example computer system in which embodiments can be implemented.

FIG. 17 is a block diagram that illustrates a computer system 100 which can assist in implementing the methods and flows disclosed herein. Computer system 100 includes a bus 102 or other communication mechanism configured to communicate information, and a processor 104 (or multiple processors 104 and 105) coupled with bus 102 configured to process information. Computer system 100 also includes a main memory 106, such as a random access memory (RAM) or other dynamic storage device, coupled to bus 102 to store information and instructions to be executed by processor 104. Main memory 106 also may be used to store temporary variables or other intermediate information during execution of instructions to be executed by processor 104. Computer system 100 further includes a read only memory (ROM) 108 or other static storage device coupled to bus 102 to store static information and instructions for processor 104. A storage device 110, such as a magnetic disk or optical disk, is provided and coupled to bus 102 to store information and instructions.

Computer system 100 may be coupled via bus 102 to a display 112, such as a cathode ray tube (CRT) or flat panel or touch panel display, to display information to a computer user. An input device 114, including alphanumeric and other keys, is coupled to bus 102 to communicate information and command selections to processor 104. Another type of user input device is cursor control 116, such as a mouse, a trackball, or cursor direction keys, to communicate direction information and command selections to processor 104 and to control cursor movement on display 112. A touch panel (screen) display may also be used as an input device.

According to one embodiment, portions of the process may be performed by computer system 100 in response to processor 104 executing one or more sequences of one or more instructions contained in main memory 106. Such instructions may be read into main memory 106 from another computer-readable medium, such as storage device 110. Execution of the sequences of instructions contained in main memory 106 causes processor 104 to perform the process steps described herein. One or more processors in a multi-processing arrangement may also be employed to execute the sequences of instructions contained in main memory 106. In alternative embodiments, hard-wired circuitry may be used in place of or in combination with software instructions. Thus, embodiments are not limited to any specific combination of hardware circuitry and software.

The term "computer-readable medium" as used herein refers to any medium that participates in providing instructions to processor 104 for execution. Such a medium may take many forms, including but not limited to, non-volatile media, volatile media, and transmission media. Non-volatile media include, for example, optical or magnetic disks, such as storage device 110. Volatile media include dynamic memory, such as main memory 106. Transmission media include coaxial cables, copper wire and fiber optics, including the wires that comprise bus 102. Transmission media can also take the form of acoustic or light waves, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 104 for execution. For example, the instructions may initially be borne on a magnetic disk of a remote computer. The remote computer can load the instructions into its dynamic memory and send the instructions over a telephone line using a modem. A modem local to computer system 100 can receive the data on the telephone line and use an infrared transmitter to convert the data to an infrared signal. An infrared detector coupled to bus 102 can receive the data carried in the infrared signal and place the data on bus 102. Bus 102 carries the data to main memory 106, from which processor 104 retrieves and executes the instructions. The instructions received by main memory 106 may optionally be stored on storage device 110 either before or after execution by processor 104.

Computer system 100 may also include a communication interface 118 coupled to bus 102. Communication interface 118 provides a two-way data communication coupling to a network link 120 that is connected to a local network 122. For example, communication interface 118 may be an integrated services digital network (ISDN) card or a modem to provide a data communication connection to a corresponding type of telephone line. As another example, communication interface 118 may be a local area network (LAN) card to provide a data communication connection to a compatible LAN. Wireless links may also be implemented. In any such implementation, communication interface 118 sends and receives electrical, electromagnetic or optical signals that carry digital data streams representing various types of information.

Network link 120 typically provides data communication through one or more networks to other data devices. For example, network link 120 may provide a connection through local network 122 to a host computer 124 or to data equipment operated by an Internet Service Provider (ISP) 126. ISP 126 in turn provides data communication services through the worldwide packet data communication network, now commonly referred to as the "Internet" 128. Local network 122 and Internet 128 both use electrical, electromagnetic or optical signals that carry digital data streams. The signals through the various networks and the signals on network link 120 and through communication interface 118, which carry the digital data to and from computer system 100, are examples of forms of carrier waves transporting the information.

Computer system 100 can send messages and receive data, including program code, through the network(s), network link 120, and communication interface 118. In the Internet example, a server 130 might transmit a requested code for an application program through Internet 128, ISP 126, local network 122 and communication interface 118. In accordance with one or more embodiments, one such downloaded application provides for the illumination optimization of the embodiment, for example. The received code may be executed by processor 104 as it is received, and/or stored in storage device 110, or other non-volatile storage for later execution. In this manner, computer system 100 may obtain application code in the form of a carrier wave.

While embodiments herein have focused on metrology targets to measure overlay, the description here may also apply, with modifications as appropriate, to, e.g., substrate and/or patterning device alignment in a lithographic apparatus using an alignment mark.

Further, embodiments have been described herein in relation to diffraction-based metrology, which, for example, measures the relative position of overlapping periodic structures from the intensity from the diffracted orders. However, embodiments herein may be applied, with appropriate modification where needed, to image-based metrology, which, for example, measures the relative position from target 1 in layer 1 to target 2 in layer 2 using high-quality images of the targets. Usually these targets are periodic structures or "boxes" (Box-in-Box (BiB)).

While the concepts disclosed herein may be used for imaging on a substrate such as a silicon wafer, it shall be understood that the disclosed concepts may be used with any type of lithographic imaging systems, e.g., those used for imaging on substrates other than silicon wafers.

Although specific reference may be made in this text to the use of the embodiments in the manufacture of ICs, it should be explicitly understood that the embodiments has many other possible applications, For example, it may be employed in the manufacture of integrated optical systems, guidance and detection patterns for magnetic domain memories, liquid-crystal display panels, thin-film magnetic heads, etc. The skilled artisan will appreciate that, in the context of such alternative applications, any use of the terms "reticle," "wafer" or "die" in this text should be considered as interchangeable with the more general terms "mask," "substrate" and "target portion," respectively.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The term "optimizing" and "optimization" as used herein mean adjusting a lithographic apparatus such that results and/or processes of lithography have more desirable characteristics, such as higher accuracy of projection of design layouts on a substrate, larger process windows, etc.

Aspects of the disclosure can be implemented in any convenient form. For example, an embodiment may be implemented by one or more appropriate computer programs which may be carried on an appropriate carrier medium which may be a tangible carrier medium (e.g. a disk) or an intangible carrier medium (e.g. a communications signal). An embodiment may be implemented using suitable apparatus which may specifically take the form of a programmable computer running a computer program arranged to implement a method as described herein.

Although specific reference may have been made above to the use of an embodiment in the context of optical lithography, it will be appreciated that the disclosure may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

Embodiments of the invention may further be described using the following clauses:

1. A method to determine an overlay error between a first structure and a second structure, wherein the first structure and second structures are on different layers on a substrate and are imaged onto the substrate by a lithographic process, the method comprising:
   obtaining an apparent overlay error;
   obtaining a systematic error caused by a factor other than misalignment of the first and second structures; and
   determining the overlay error by removing the systematic error from the apparent overlay error.
2. The method of clause 1, wherein obtaining the systematic error comprises determining the systematic error after the first structure is fabricated and before the second structure is fabricated.
3. The method of clause 1, wherein obtaining the systematic error comprises determining the systematic error after both the first and second structures are fabricated.

4. The method of clause 1, wherein part of the first structure but not part of the second structure is in a first area, wherein parts of both the first and second structures are in a third area.

5. The method of clause 4, wherein part of the second structure but not part of the first structure is in a second area.

6. The method of clause 4, wherein obtaining the systematic error comprises obtaining apparent a characteristic of diffraction orders of both the first and second structures in the third area, and a characteristic of the first structure in the first area.

7. The method of clause 5, wherein obtaining the systematic error comprises obtaining apparent a characteristic of diffraction orders of both the first and second structures in the third area, a characteristic of the first structure in the first area, and a characteristic of the second structure in the second area.

8. The method of clause 6 or clause 7, wherein the characteristic of the first structure comprises periodicity, shape, size or a combination thereof, of the first structure; or wherein the characteristic of the second structure comprises periodicity, shape, size or a combination thereof, of the second structure.

9. The method of any of clauses 1 to 8, wherein the first structure is a first grating at least partially overlapping the second structure, and/or wherein the second structure is a second grating at least partially overlapped by the first structure.

10. The method of any of clauses 1 to 9, wherein obtaining the apparent overlay error comprises interpolating or extrapolating from a fitted curve.

11. The method of any of clauses 1 to 10, further comprising adjusting a characteristic of the lithographic process based on the overlay error.

12. A method to determine an overlay error between a first structure and a second structure, wherein the first structure and second structures are on different layers on a substrate and are imaged onto the substrate by a lithographic process, the method comprising:
    obtaining an apparent characteristic of diffraction orders of diffraction by an overlapping portion of the first and second structures;
    obtaining a corrected characteristic of the diffraction order; and
    determining the overlay error from the corrected characteristic.

13. The method of clause 12, wherein obtaining the corrected characteristic comprises subtracting from the apparent characteristic a contribution of a factor other than misalignment of the first and second structures.

14. The method of clause 12, wherein obtaining the corrected characteristic comprises determining the contribution after the first structure is fabricated and before the second structure is fabricated.

15. The method of clause 12, wherein obtaining the corrected characteristic comprises determining the contribution after both the first and second structures are fabricated.

16. The method of clause 12, wherein part of the first structure but not part of the second structure is in a first area, wherein parts of both the first and second structures are in a third area.

17. The method of clause 16, wherein part of the second structure but not part of the first structure is in a second area.

18. The method of clause 17, wherein obtaining the corrected characteristic further comprises measuring the contribution in the first area, the second area, or both.

19. The method of any of clauses 12 to 18, wherein the first structure is a first grating at least partially overlapping the second structure, and/or wherein the second structure is a second grating at least partially overlapped by the first structure.

20. The method of any of clauses 12 to 19, wherein obtaining the apparent characteristic comprises optically measuring diffraction.

21. The method of any of clauses 12 to 20, further comprising adjusting a characteristic of the lithographic process based on the overlay error.

22. A computer program product comprising a non-transitory computer readable medium having instructions recorded thereon, the instructions when executed by a computer implementing the method of any of the preceding clauses.

The foregoing description of the specific embodiments reveals the general nature of the disclosure such that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The descriptions above are intended to be illustrative, not limiting. The breadth and scope of the present invention should not be limited by any of the above-described exemplary embodiments, but should be defined only in accordance with the following claims and their equivalents. Thus, it will be apparent to one skilled in the art that modifications may be made to the embodiments as described without departing from the scope of the claims set out below.

What is claimed is:

1. A method to determine an overlay error between a first structure and a second structure, wherein the first structure and second structures are on different layers on a substrate and are imaged onto the substrate by a lithographic process, the method comprising:
    obtaining an apparent overlay error;
    obtaining a systematic error caused by a factor other than misalignment of the first and second structures, the systematic error determined based on a measurement of a pattern in the layer of the first structure and based on a separate measurement of a pattern in the layer of the second structure; and
    determining the overlay error by removing the systematic error from the apparent overlay error.

2. The method of claim 1, wherein obtaining the systematic error comprises determining the systematic error based on the measurement of the pattern in the layer of the first structure after the first structure is fabricated and before the second structure is fabricated.

3. The method of claim 1, wherein obtaining the systematic error comprises determining the systematic error based on the measurement of the pattern in the layer of the first structure and the pattern in the layer of the second structure after both the first and second structures are fabricated.

4. The method of claim 1, wherein part of the first structure but not part of the second structure is in a first area, wherein the part of the first structure corresponds to the pattern in the layer of the first structure, and wherein parts of both the first and second structures are in a third area.

5. The method of claim 4, wherein part of the second structure but not part of the first structure is in a second area, and wherein the part of the second structure corresponds to the pattern in the layer of the second structure.

6. The method of claim 4, wherein obtaining the systematic error comprises obtaining an apparent characteristic of diffraction orders of both the first and second structures in the third area, and a characteristic of the first structure in the first area, the characteristic of the first structure comprising a geometrical characteristic of the first structure in the first area and/or a characteristic of diffraction orders of the first structure in the first area.

7. The method of claim 5, wherein obtaining the systematic error comprises obtaining an apparent characteristic of diffraction orders of both the first and second structures in the third area, a characteristic of the first structure in the first area, and a characteristic of the second structure in the second area, wherein the characteristic of the first structure comprises a geometrical characteristic of the first structure in the first area and/or a characteristic of diffraction orders of the first structure in the first area and the characteristic of the second structure comprises a geometrical characteristic of the second structure in the second area and/or a characteristic of diffraction orders of the second structure in the second area.

8. The method of claim 6, wherein the characteristic of the first structure comprises periodicity, shape, size or a combination selected therefrom, of the first structure.

9. The method of claim 1, wherein obtaining the apparent overlay error comprises interpolating or extrapolating from a fitted curve.

10. The method of claim 1, further comprising adjusting a characteristic of the lithographic process based on the overlay error.

11. The method of claim 1, wherein the measurement of the first and second patterns are obtained from a common illumination of both patterns by a measurement beam.

12. A method to determine an overlay error between a first structure and a second structure, wherein the first structure and second structure are on different layers on a substrate and are imaged onto the substrate by a lithographic process, the method comprising:
   obtaining an apparent characteristic of diffraction orders of diffraction by an overlapping portion of the first and second structures;
   obtaining a corrected characteristic of the diffraction orders, the corrected characteristic determined based on a measurement of a pattern in the layer of the first structure and from a separate measurement of a pattern in the layer of the second structure; and
   determining the overlay error from the corrected characteristic.

13. The method of claim 12, wherein obtaining the corrected characteristic comprises subtracting from the apparent characteristic a contribution of a factor other than misalignment of the first and second structures.

14. The method of claim 13, wherein obtaining the corrected characteristic comprises determining the contribution based on the measurement of the pattern in the layer of the first structure after the first structure is fabricated and before the second structure is fabricated.

15. The method of claim 13, wherein obtaining the corrected characteristic comprises determining the contribution based on the measurement of the pattern in the layer of the first structure and the pattern in the layer of the second structure after both the first and second structures are fabricated.

16. The method of claim 12, wherein part of the first structure but not part of the second structure is in a first area, wherein the part of the first structure corresponds to the pattern in the layer of the first structure, and wherein parts of both the first and second structures are in a third area.

17. The method of claim 12, wherein obtaining the apparent characteristic comprises optically measuring diffraction.

18. The method of claim 12, further comprising adjusting a characteristic of the lithographic process based on the overlay error.

19. A computer program product comprising a non-transitory computer readable medium having instructions recorded thereon, the instructions configured to cause a computer system to:
   obtain an apparent overlay error between a first structure and a second structure, wherein the first structure and second structures are on different layers on a substrate and are imaged onto the substrate by a lithographic process;
   obtain a systematic error caused by a factor other than misalignment of the first and second structures, the systematic error determined based on a measurement of a pattern in the layer of the first structure and based on a separate measurement of a pattern in the layer of the second structure; and
   determine an overlay error by removing the systematic error from the apparent overlay error.

20. A computer program product comprising a non-transitory computer readable medium having instructions recorded thereon, the instructions configured to cause a computer system to:
   obtain an apparent characteristic of diffraction orders of diffraction by an overlapping portion of first and second structures, wherein the first structure and second structure are on different layers on a substrate and are imaged onto the substrate by a lithographic process;
   obtain a corrected characteristic of the diffraction orders, the corrected characteristic determined based on a measurement of a pattern in the layer of the first structure and from a separate measurement of a pattern in the layer of the second structure; and
   determine an overlay error between the first structure and the second structure from the corrected characteristic.

* * * * *